United States Patent
Price et al.

(10) Patent No.: US 10,064,752 B2
(45) Date of Patent: Sep. 4, 2018

(54) MOTORIZED SUPRACHOROIDAL INJECTION OF THERAPEUTIC AGENT

(71) Applicant: ORBIT BIOMEDICAL LIMITED, London (GB)

(72) Inventors: Daniel W. Price, Loveland, OH (US); Isaac J. Khan, Bridgewater, NJ (US); Brendan J. Oberkircher, Cincinnati, OH (US); Saeed Sokhanvar, Belmont, MA (US); Daniel J. Yasevac, Somerville, MA (US); Michel Bruehwiler, Newton, MA (US); Leah R. Soffer, Somerville, MA (US); Mohammadreza Ramerzanifard, Watertown, MA (US); Mary Carter, Cambridge, MA (US)

(73) Assignee: ORBIT BIOMEDICAL LIMITED, London (GB)

(*) Notice: Subject to any disclaimer, the term of this patent is extended or adjusted under 35 U.S.C. 154(b) by 386 days.

(21) Appl. No.: 14/840,622

(22) Filed: Aug. 31, 2015

(65) Prior Publication Data
US 2016/0074217 A1    Mar. 17, 2016

Related U.S. Application Data

(60) Provisional application No. 62/049,118, filed on Sep. 11, 2014.

(51) Int. Cl.
*A61F 9/00* (2006.01)
*A61M 5/32* (2006.01)
(Continued)

(52) U.S. Cl.
CPC ........ *A61F 9/0017* (2013.01); *A61F 9/00736* (2013.01); *A61M 5/3287* (2013.01);
(Continued)

(58) Field of Classification Search
CPC .... A61F 9/0008; A61F 9/0017; A61F 9/0026; A61F 9/007; A61F 9/00736
See application file for complete search history.

(56) References Cited

U.S. PATENT DOCUMENTS 6,309,374 B1    10/2001  Hecker et al.
7,413,734 B2    8/2008   Mistry et al.
(Continued)

FOREIGN PATENT DOCUMENTS

WO    WO 02/17986 A2    3/2002
WO    WO 2016/040635 A1  9/2014

OTHER PUBLICATIONS

International Search Report and Written Opinion dated Jan. 15, 2016 for Application No. PCT/US2015/049430, 11 pgs.
(Continued)

*Primary Examiner* — Aarti B Berdichevsky
(74) *Attorney, Agent, or Firm* — Frost Brown Todd LLC

(57) ABSTRACT

An apparatus for delivering therapeutic agent to an eye comprises a body, a cannula, a hollow needle, and an automated actuation assembly. The cannula extends distally from the body and is sized and configured to be insertable between a choroid and a sclera of a patient's eye. The actuation assembly is operable to actuate the needle relative to the cannula to thereby drive a distal portion of the needle along an exit axis that is obliquely oriented relative to the longitudinal axis of the cannula. The cannula may be inserted through a sclerotomy to position a distal end of the cannula at a posterior region of the eye, between the choroid and sclera. The needle may be advanced through the choroid to deliver the therapeutic agent adjacent to the potential space between the neurosensory retina and the retinal pigment epithelium layer, adjacent to the area of geographic atrophy.

20 Claims, 37 Drawing Sheets

(51) Int. Cl.
  *A61M 5/158* (2006.01)
  *A61F 9/007* (2006.01)
(52) U.S. Cl.
  CPC ............. *A61F 9/007* (2013.01); *A61F 9/0008*
    (2013.01); *A61F 9/0026* (2013.01); *A61M 5/32*
      (2013.01); *A61M 2005/1585* (2013.01)

(56) References Cited

U.S. PATENT DOCUMENTS

| | | |
|---|---|---|
| 2004/0199130 A1 | 10/2004 | Chornenky et al. |
| 2010/0010504 A1 | 1/2010 | Simann et al. |
| 2015/0223977 A1 | 8/2015 | Oberkircher et al. |

OTHER PUBLICATIONS

International Preliminary Report on Patentability dated Mar. 14, 2017 for Application No. PCT/US2015/049430, 7 pgs.
U.S. Appl. No. 62/049,118, filed Sep. 11, 2014.

MOTORIZED SUPRACHOROIDAL INJECTION OF THERAPEUTIC AGENT

PRIORITY

This application claims priority to U.S. Provisional Patent Application No. 62/049,118, entitled "Suprachoroidal Motorized Needle Advance Injector," filed Sep. 11, 2014, the disclosure of which is incorporated by reference herein.

JOINT RESEARCH STATEMENT

Subject matter disclosed in this application was developed and the claimed invention was made by, or on behalf of, one or more parties to a joint research agreement that was in effect on or before the effective filing date of the claimed invention. The claimed invention was made as a result of activities undertaken within the scope of the joint research agreement. The parties to the joint research agreement include Ethicon Endo-Surgery, Inc. and Janssen Research & Development, LLC.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and in some cases may disappear as well. It may therefore be desirable to provide treatment for macular degeneration in order to prevent or reverse the loss of vision caused by macular degeneration. In some cases it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

DETAILED DESCRIPTION

Figure 1:
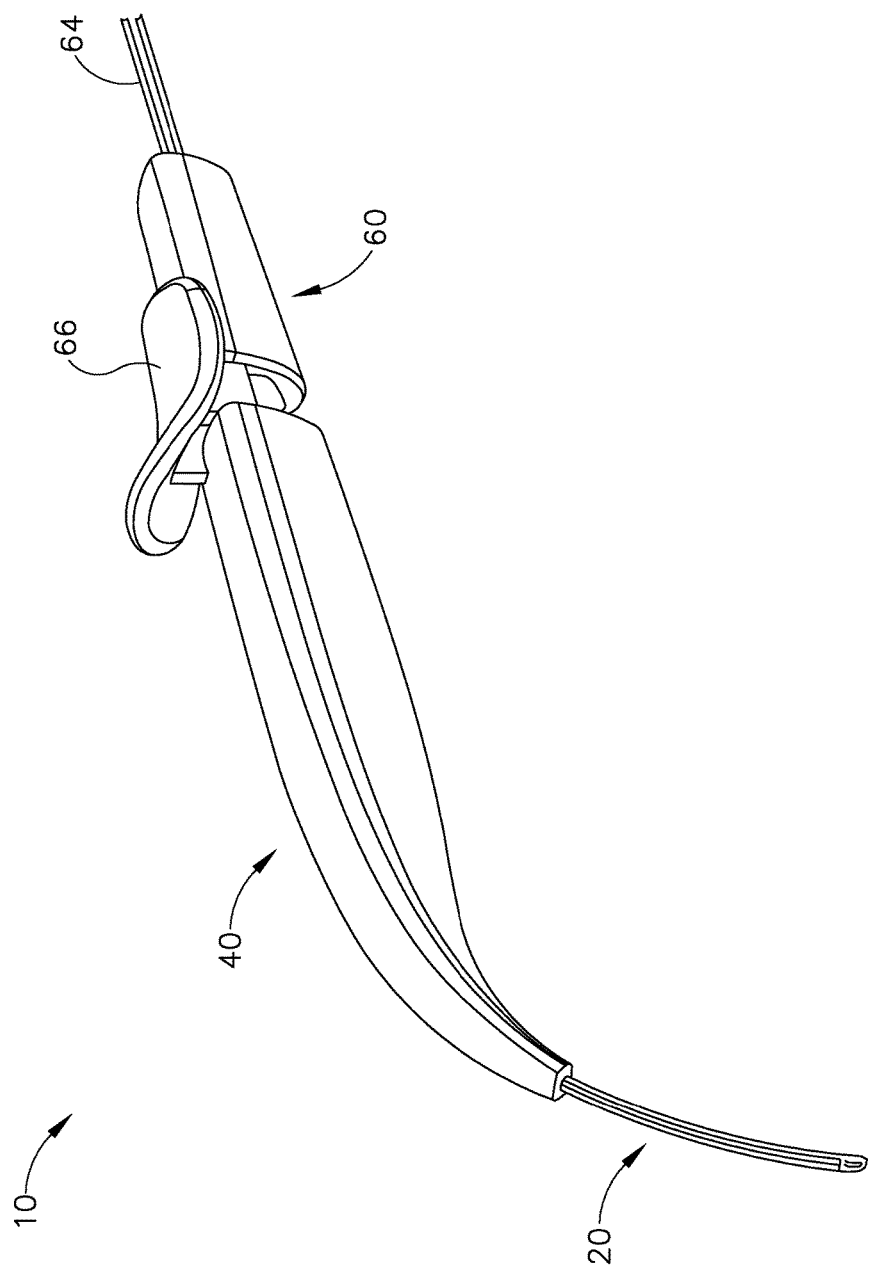
FIG. 1 depicts a perspective view of an exemplary instrument for subretinal administration of a therapeutic agent from a suprachoroidal approach.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Instrument with Slider Articulation Feature

FIGS. 1-4 show an exemplary instrument (10) that is configured for use in a procedure for the subretinal administration of a therapeutic agent to an eye of a patient from a suprachoroidal approach. Instrument (10) comprises a flexible cannula (20), a body (40), and a slidable (60). Cannula (20) extends distally from body (40) and has a generally rectangular cross section. Cannula (20) is generally configured to support a needle (30) that is slidable within cannula (20), as will be described in greater detail below.

In the present example, cannula (20) comprises a flexible material such as Polyether block amide (PEBA), which may be manufactured under the trade name PEBAX. Of course, any other suitable material or combination of materials may be used. Also in the present example, cannula (20) has a cross-sectional profile dimension of approximately 2.0 mm by 0.8 mm, with a length of approximately 80 mm. Alternatively, any other suitable dimensions may be used.

As will be described in greater detail below, cannula (20) is flexible enough to conform to specific structures and contours of the patient's eye, yet cannula (20) has sufficient column strength to permit advancement of cannula (20) between the sclera and choroid of patient's eye without buckling. Several factors may contribute to suitable flexibility of cannula (20). For instance, the durometer of the material used to construct cannula (20) at least partially characterizes the flexibility of cannula (20). By way of example only, the material that is used to form cannula (20) may have a shore hardness of approximately 27 D, approximately 33 D, approximately 42 D, approximately 46 D, or any other suitable shore hardness. It should be understood that the shore hardness may fall within the range of approximately 27 D to approximately 46 D; or more particularly within the range of approximately 33 D to approximately 46 D; or more particularly within the range of approximately 40 D to approximately 45 D. The particular cross-sectional shape of cannula (20) may also at least partially characterize the flexibility of cannula (20). Additionally, the stiffness of needle (30) disposed within cannula (20) may at least partially characterize the flexibility of cannula (20).

In the present example, the flexibility of cannula (20) may be quantified by calculating a flexural stiffness for cannula (20). Flexural stiffness is calculated by the product of the elastic modulus and the area moment of inertia. By way of example only, one exemplary material that may be used to form cannula (20) may have a shore hardness of D27, an elastic modulus (E) of $1.2 \times 10^7$ N/m², and an area moment of inertia ($I_x$) of $5.52 \times 10^{-14}$ m⁴, providing a calculated flexural stiffness about the x-axis at $0.7 \times 10^{-6}$ Nm². Another exemplary material that may be used to form cannula (20) may have a shore hardness of D33, an elastic modulus (E) of $2.1 \times 10^7$ N/m², and an area moment of inertia ($I_x$) of $5.52 \times 10^{-14}$ m⁴, providing a calculated flexural stiffness about the x-axis at $1.2 \times 10^{-6}$ Nm². Another exemplary material that may be used to form cannula (20) may have a shore hardness of D42, an elastic modulus (E) of $7.7 \times 10^7$ N/m², and an area moment of inertia ($I_x$) of $5.52 \times 10^{-14}$ m⁴, providing a calculated flexural stiffness about the x-axis at $4.3 \times 10^{-6}$ Nm². Another exemplary material that may be used to form cannula (20) may have a shore hardness of D46, an elastic modulus (E) of $17.0 \times 10^7$ N/m², and an area moment of inertia ($I_x$) of $5.52 \times 10^{-14}$ m⁴, providing a calculated flexural stiffness about the x-axis at $9.4 \times 10^{-6}$ Nm². Thus, by way of example only, the flexural stiffness of cannula (20) may fall within the range of approximately $0.7 \times 10^{-6}$ Nm² to approximately $9.4 \times 10^{-6}$ Nm²; or more particularly within the range of approximately $1.2 \times 10^{-6}$ Nm² to approximately $9.4 \times 10^{-6}$ Nm²; or more particularly within the range of approximately $2.0 \times 10^{-6}$ Nm² to approximately $7.5 \times 10^{-6}$ Nm²; or more particularly within the range of approximately $2.0 \times 10^{-6}$ Nm² to approximately $6.0 \times 10^{-6}$ Nm²; or more particularly within the range of approximately $3.0 \times 10^{-6}$ Nm² to approximately $5.0 \times 10^{-6}$ Nm²; or more particularly within the range of approximately $4.0 \times 10^{-6}$ Nm² to approximately $5.0 \times 10^{-6}$ Nm².

In the present example, the flexibility of cannula (20) may also be quantified by the following formula:

$$\delta = \frac{FL^3}{48EI} \quad (1)$$

In the above equation, flexural stiffness (EI) is calculated experimentally by deflecting cannula (20) having a fixed span (L) a set distance to yield a predetermined amount of deflection (δ). The amount of force (F) required for such a deflection may then be recorded. For instance, when using such a method cannula (20) may have a span of 0.06 m and may be deflected for a given distance. By way of example only, one exemplary material that may be used to form cannula (20) may require a force of 0.0188 N to achieve a deflection of 0.0155 m, providing a calculated flexural stiffness about the x-axis of $5.5 \times 10^{-6}$ Nm². In another exemplary material that may be used to form cannula (20) may require a force of 0.0205 N to achieve a deflection of 0.0135 m, providing a calculated flexural stiffness about the x-axis of $6.8 \times 10^{-6}$ Nm². In still another exemplary material that may be used to form cannula (20) may require a force of 0.0199 N to achieve a deflection of 0.0099 m, providing a calculated flexural stiffness about the x-axis of $9.1 \times 10^{-6}$ Nm². In yet another exemplary material that may be used to form cannula (20) may require a force of 0.0241 N to achieve a deflection of 0.0061 m, providing a calculated flexural stiffness about the x-axis of $1.8 \times 10^{-6}$ Nm². In yet another exemplary material that may be used to form cannula (20) may require a force of 0.0190 N to achieve a deflection 0.0081 m, providing a calculated flexural stiffness about the x-axis of $1.0 \times 10^{-6}$ Nm². In yet another exemplary material that may be used to form cannula (20) may require a force of 0.0215 N to achieve a deflection of 0.0114 m, providing a calculated flexural stiffness about the x-axis of $8.4 \times 10^{-6}$ Nm². In yet another exemplary material that may be used to form cannula (20) may require a force of 0.0193 N to achieve a deflection of 0.0170 m, providing a calculated flexural stiffness about the x-axis of $5.1 \times 10^{-6}$ Nm². In yet another exemplary material that may be used to form cannula (20) may require a force of 0.0224 N to achieve a deflection of 0.0152 m, providing a calculated flexural stiffness about the x-axis of $6.6 \times 10^{-6}$ Nm². In yet another exemplary material that may be used to form cannula (20) may require a force of 0.0183 N to achieve a deflection of 0.0119 m, providing a calculated flexural stiffness about the x-axis of $6.9 \times 10^{-6}$ Nm². In yet another exemplary material that may be used to form cannula (20) may require a force of 0.0233 N to achieve a deflection of 0.0147 m, providing a calculated flexural stiffness about the x-axis of $7.1 \times 10^{-6}$ Nm². In yet another exemplary material that may be used to form cannula (20) may require a force of 0.0192 N to achieve a deflection of 0.0122, providing a calculated flexural stiffness about the x-axis of $7.1 \times 10^{-6}$ Nm². In yet another exemplary material that may be used to form cannula (20) may require a force of 0.0201 N to achieve a deflection of 0.0201, providing a calculated flexural stiffness about the x-axis of $4.5 \times 10^{-6}$ Nm². Thus, by way of example only, the flexural stiffness of cannula (20) may fall within the range of approximately $1.0 \times 10^{-6}$ Nm² to approximately $9.1 \times 10^{-6}$ Nm². It should be understood that in other examples, the flexural stiffness of cannula may fall within the range of approximately $0.7 \times 10^{-6}$ Nm² to approximately $11.1 \times 10^{-6}$ Nm²; or more particularly within the range of approximately $2.0 \times 10^{-6}$ Nm² to approximately $6.0 \times 10^{-6}$ Nm².

Needle (30) may have a flexural stiffness that differs from the flexural stiffness of cannula (20). By way of example only, needle (30) may be formed of a nitinol material that has an elastic modulus (E) of $7.9 \times 10^{10}$ N/m², and an area moment of inertia ($I_x$) of $2.12 \times 10^{-17}$ m⁴, providing a calculated flexural stiffness about the x-axis at $1.7 \times 10^{-6}$ Nm². By way of further example only, the flexural stiffness of needle (30) may fall within the range of approximately $0.5 \times 10^{-6}$ Nm² to approximately $2.5 \times 10^{-6}$ Nm²; or more particularly within the range of approximately $0.75 \times 10^{-6}$ Nm² to approximately $2.0 \times 10^{-6}$ Nm²; or more particularly within the range of approximately $1.25 \times 10^{-6}$ Nm² to approximately $1.75 \times 10^{-6}$ Nm².

Figure 5:
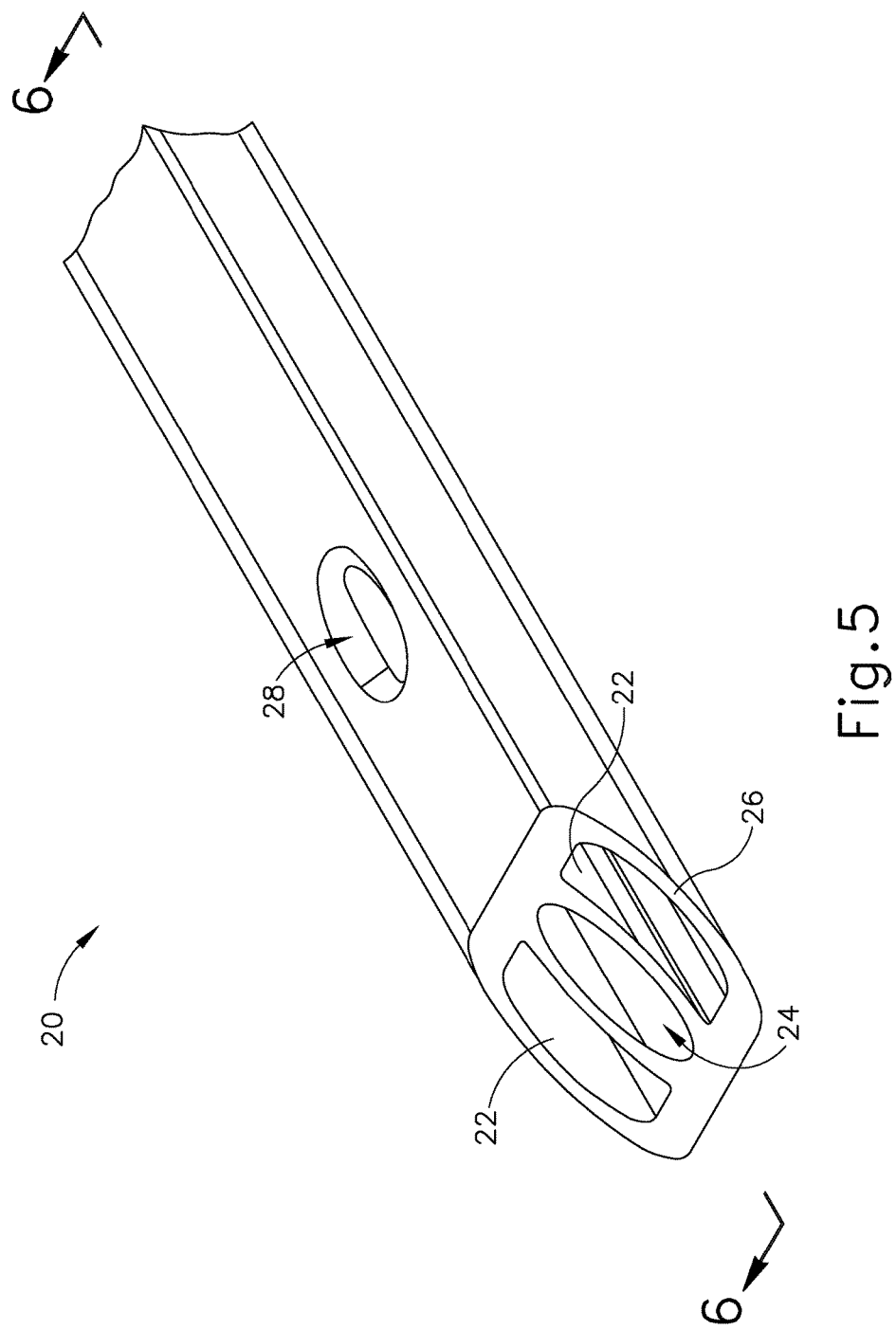
FIG. 5 depicts a perspective view of the distal end of an exemplary cannula that may be incorporated into the instrument of FIG. 1.
Figure 6:
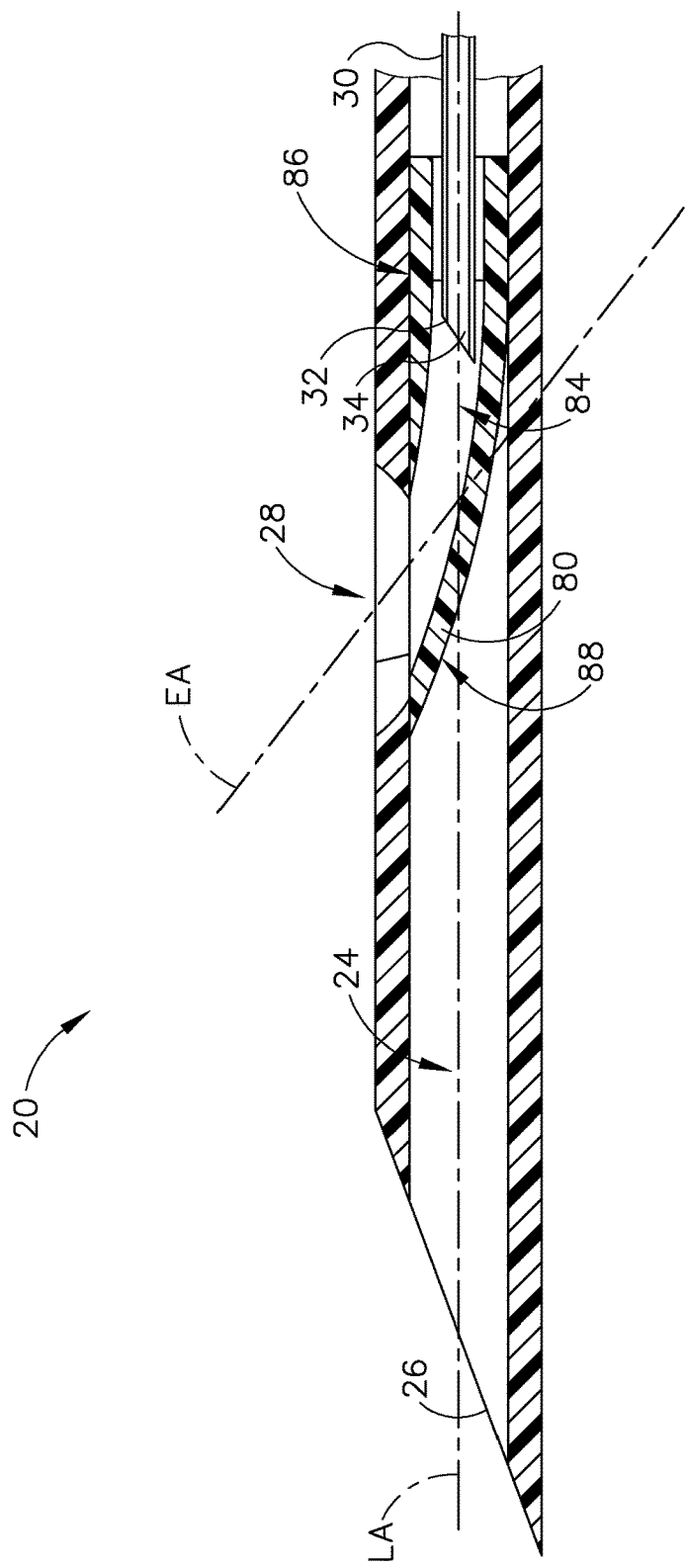
FIG. 6 depicts a cross-sectional view of the cannula of FIG. 5, with the cross-section taken along line 6-6 of FIG. 5.

As can be seen in FIGS. 5 and 6, cannula (20) comprises two side lumens (22) and a single central lumen (24) extending longitudinally through cannula (20) and terminating at an atraumatic, beveled distal end (26). A beveled lateral opening (28) is located proximal to beveled distal end (26). Side lumens (22) contribute to the flexibility of cannula (20). Although lumens (22, 24) are shown as being open at beveled distal end (26), it should be understood that in some examples, side lumens (22, 24) may be optionally closed at beveled distal end (26). As will be described in greater detail below, central lumen (24) is configured to receive needle (30) and a needle guide (80). In some versions, an optical fiber (not shown) is also disposed in central lumen (24) alongside needle (30). Such an optical fiber may be used to provide illumination and/or optical feedback.

Beveled distal end (26) is generally beveled to provide separation between the sclera and choroid layers to enable cannula (20) to be advanced between such layers while not inflicting trauma to the sclera or choroid layers. In the present example, beveled distal end (26) is beveled at an angle of approximately 15° relative to the longitudinal axis of cannula (20) in the present example. In other examples, beveled distal end (26) may have a bevel angle within the range of approximately 5° to approximately 50°; or more particularly within the range of approximately 5° to approximately 40°; or more particularly within the range of approximately 10° to approximately 30°; or more particularly within the range of approximately 10° to approximately 20°. In some other versions, distal end (26) is rounded instead of being beveled. Alternatively, distal end (26) may have any other suitable configuration.

A needle guide (80) is disposed within lumen (24) such that the distal end of needle guide (80) abuts beveled lateral opening (28). Needle guide (80) is generally configured to direct needle (30) upwardly along an exit axis (EA) that is obliquely oriented relative to the longitudinal axis (LA) of cannula (20) through beveled opening (28) of cannula (20). Needle guide (80) may be formed of plastic, stainless steel, and/or any other suitable biocompatible material(s). The shape of needle guide (80) is configured for insertion into central lumen (24). In the present example, needle guide (80) is secured within central lumen (24) by a press or interference fit, although in other examples, adhesives and/or mechanical locking mechanisms may be used to secure needle guide (80).

As can best be seen in FIG. 6, needle guide (80) defines an internal lumen (84) that is configured to slidably receive needle (30). In particular, internal lumen (84) includes a generally straight proximal portion (86) and a curved distal portion (88). Straight proximal portion (86) corresponds to the longitudinal axis (LA) of cannula (20), while curved distal portion (88) curves upwardly away from the longitudinal axis of cannula (20). Curved distal portion (88) of the present example is curved to direct needle (30) along an exit axis (EA) that extends distally from cannula (20) at an angle of approximately 7° to approximately 9° relative to the longitudinal axis (LA) of cannula (20). It should be understood that such an angle may be desirable to deflect needle (30) in a direction to ensure penetration of needle into the choroid (306) and to minimize the possibility of needle (30) continuing beneath the choroid (306) through the suprachoroidal space (as opposed to penetrating through the choroid (306)) and the possibility of retinal perforation. By way of further example only, curved distal portion (88) may urge needle (30) to exit cannula (20) along an exit axis (EA) that is oriented at an angle within the range of approximately 5° to approximately 30° relative to the longitudinal axis (LA) of cannula (20); or more particularly within the range of approximately 5° to approximately 20° relative to the longitudinal axis (LA) of cannula (20); or more particularly within the range of approximately 5° to approximately 10° relative to the longitudinal axis (LA) of cannula (20).

Needle (30) has a sharp distal end (32) and defines an internal lumen (34). Distal end (32) of the present example has a lancet configuration. In some other versions, distal end (32) has a tri-bevel configuration or any other configurations as described in U.S. patent application Ser. No. 14/619,256, entitled "Method and Apparatus for Suprachoroidal Administration of Therapeutic Agent," filed Feb. 11, 2015, the disclosure of which is incorporated by reference herein. Still other suitable forms that distal end (32) may take will be apparent to those of ordinary skill in the art in view of the teachings herein. Needle (30) of the present example comprises a nitinol hypodermic needle that is sized to deliver the therapeutic agent while being small enough to create self sealing wounds as needle (30) penetrates tissue structures of the patient's eye, as will be described in greater detail below. By way of example only, needle (30) may be 35 gauge with a 100 μm inner diameter, although other suitable sizes may be used. For instance, the outer diameter of needle (30) may fall within the range of 27 gauge to 45 gauge; or more particularly within the range of 30 gauge to 42 gauge; or more particularly within the range of 32 gauge to 39 gauge. As another merely illustrative example, the inner diameter of needle (30) may fall within the range of approximately 50 μm to approximately 200 μm; or more particularly within the range of approximately 50 μm to approximately 150 μm; or more particularly within the range of approximately 75 μm to approximately 125 μm.

Referring back to FIGS. 1-2, body (40) is generally shaped as an elongate rectangle with a curved distal end. The particular shape of body (40) that is shown is configured to be grasped by an operator. Alternatively, body (40) may be mounted on a support device or robotic arm for ease of positioning instrument (10), as described in U.S. patent application Ser. No. 14/619,256, entitled "Method and Apparatus for Suprachoroidal Administration of Therapeutic Agent," filed Feb. 11, 2015, the disclosure of which is incorporated by reference herein.

Actuation assembly (60) includes an actuation member (62) and a locking member (66). Locking member (66) is removably attachable to body engagement portion (50), between body (40) and actuation member (62). As will be described in greater detail below, locking member (66) fills a space between body (40) and actuation member (62) to prevent actuation member (62) from being advanced distally relative to body (40). However, locking member (66) can be removed to selectively permit actuation member (62) to be advanced distally relative to body (40).

Figure 2:
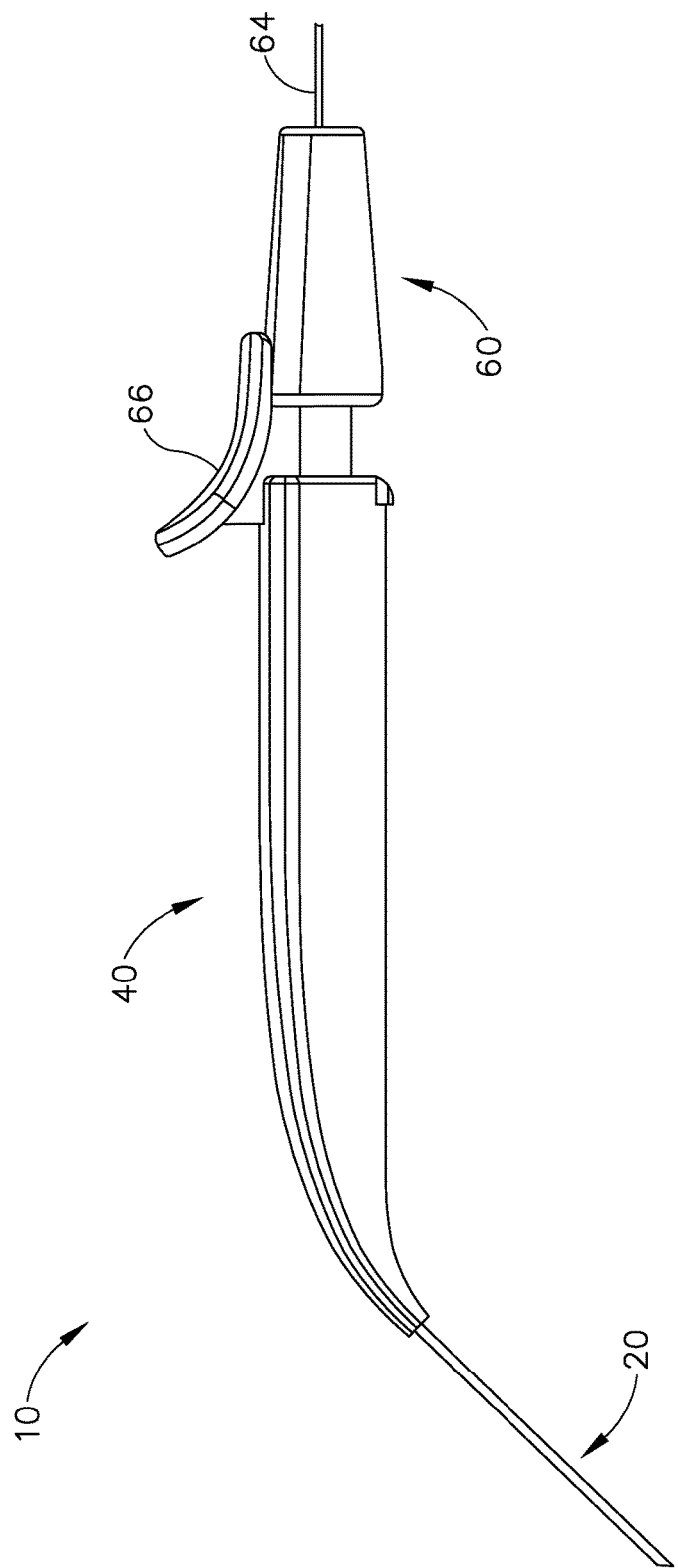
FIG. 2 depicts a side elevational view of the instrument of FIG. 1.
Figure 3:
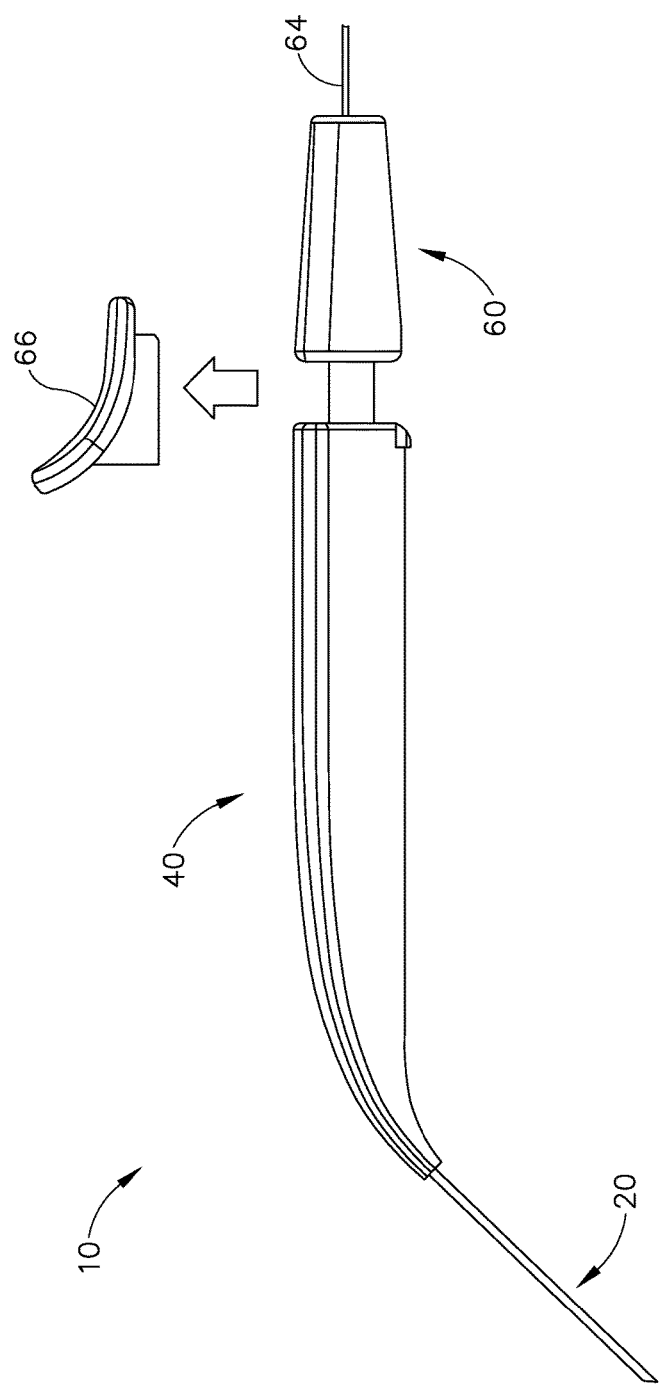
FIG. 3 depicts another side elevational view of the instrument of FIG. 1, with a locking member removed.
Figure 4:
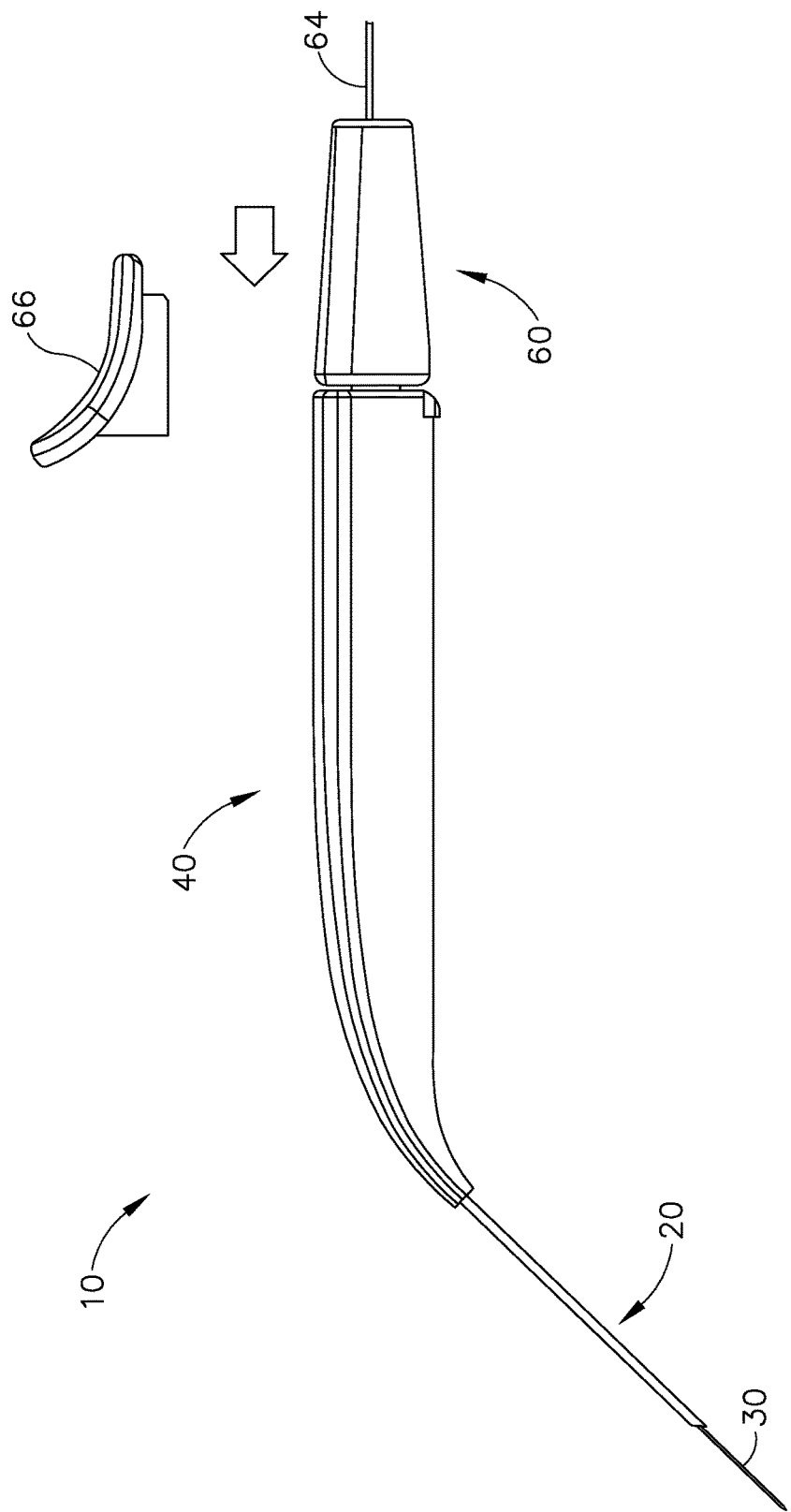
FIG. 4 depicts another side elevational view of the instrument of FIG. 1, with an actuation member advanced distally to extend the needle distally from the cannula.

FIGS. 2-4 show an exemplary actuation of instrument (10). In particular, as can be seen in FIG. 2, needle (30) is initially retracted into cannula (20) and locking member (66) is positioned between body (40) and actuation member (62), thereby preventing advancement of actuation member (62). With instrument (10) in this configuration, cannula (20) may be positioned within an eye of a patient as will be described in greater detail below.

Once cannula (20) is positioned within an eye of a patient, an operator may desire to advance needle (30) relative to cannula (20). To advance needle (30), an operator may first remove locking member (66) by pulling locking member (66) away from instrument (10), as can be seen in FIG. 3. Once locking member (66) is removed, actuation member (62) may be moved or translated relative to body (40) to advance needle (30) relative to cannula (20) as described in U.S. patent application Ser. No. 14/619,256, entitled "Method and Apparatus for Suprachoroidal Administration of Therapeutic Agent," filed Feb. 11, 2015, the disclosure of which is incorporated by reference herein. Actuation member (62) of the present example is only configured to translate needle (30) and not rotate needle (30). In other examples, it may be desirable to rotate needle (30). Accordingly, alternative examples may include features in actuation member (62) to rotate and translate needle (30).

In the present example, advancement of actuation member (62) into contact with body (40) as shown in FIG. 4 corresponds to advancement of needle (30) to a position relative to cannula (20) to a predetermined amount of penetration within an eye of a patient. In other words, instrument (10) is configured such that an operator only has to advance actuation member (62) into contact with body (40) to properly position needle (30) within an eye of a patient. In some examples, the predetermined amount of advancement of needle (30) relative to cannula (20) is between approximately 0.25 mm to approximately 10 mm; or more particularly within the range of approximately 0.1 mm to approximately 10 mm; or more particularly within the range of approximately 2 mm to approximately 6 mm; or more particularly to approximately 4 mm. In other examples, contact between actuation member (62) and body (40) may have no particular significance besides the maximum advancement of needle (30) relative to cannula (20). Instead, instrument (10) may be equipped with certain tactile feedback features to indicate to an operator when needle (30) has been advanced to certain predetermined distances relative to cannula (20). Accordingly, an operator may determine the desired depth of penetration of needle (30) into a patient's eye based on direct visualization of indicia on instrument and/or based on tactile feedback from instrument (10). Of course, such tactile feedback features may be combined with the present example, as will be apparent to those of ordinary skill in the art in view of the teachings herein.

II. Exemplary Alternative Instruments and Features

In some examples, it may be desirable to vary certain components or features of the instruments described herein. For instance, it may be desirable to utilize instruments similar to instrument (10) with alternative mechanisms to actuate needle (30). Yet in other examples, it may be desirable to utilize instruments similar to instrument (10) equipped with different cannula (20) or needle (30) geometries. Instruments having the above referenced variations may be desirable for different surgical procedures, or surgical procedures similar to the procedure discussed above, to engage tissue structures having varying physical properties. While certain examples of variations are described herein, it should be understood that the instruments described herein may include any other alternative features as will be apparent to those of ordinary skill in the art in view of the teachings herein.

Figure 7:
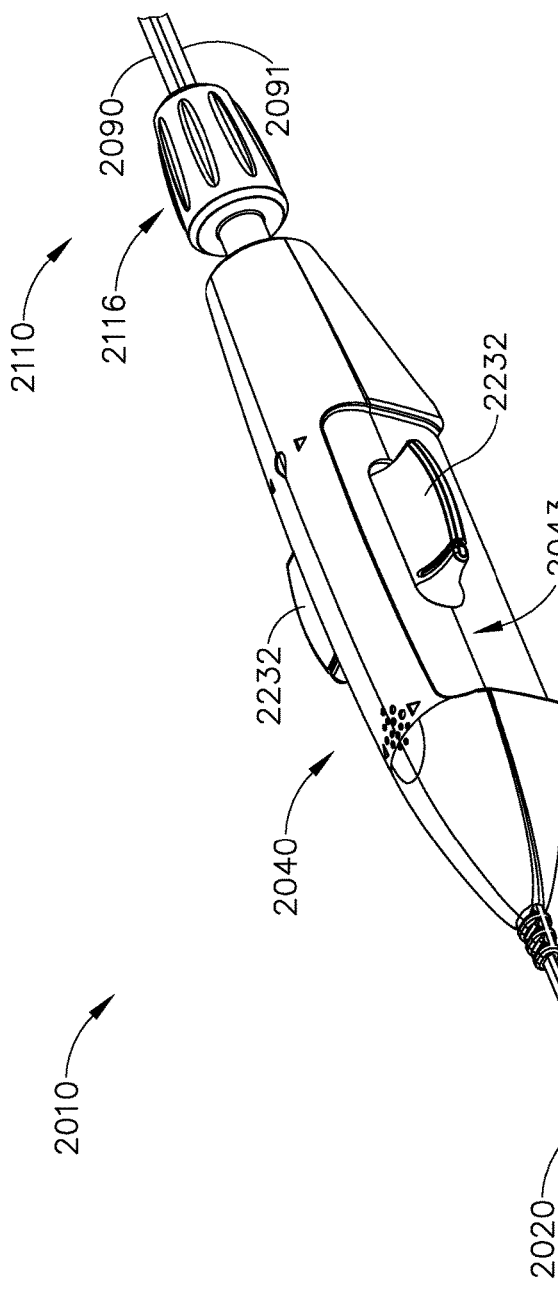
FIG. 7 depicts a perspective view of another exemplary alternative instrument for subretinal administration of a therapeutic agent from a suprachoroidal approach.

FIG. 7 shows an exemplary alternative instrument (2010) that is similar to instrument (10) described above. While certain features and operabilities of instrument (2010) are described below, it should be understood that, in addition to or in lieu of the following, instrument (2010) may be configured and/or operable in accordance with any of the teachings of U.S. patent application Ser. No. 14/619,256, entitled "Method and Apparatus for Suprachoroidal Administration of Therapeutic Agent," filed Feb. 11, 2015, the disclosure of which is incorporated by reference herein. Like with instrument (10), instrument (2010) of the present example is generally usable in the procedure described herein to deliver a therapeutic fluid subretinally to an eye of a patient from a suprachoroidal approach. It should therefore be understood that instrument (2010) may be readily used in place of instrument (10) to perform the medical procedures described herein. Like instrument (10), instrument (2010) of this example comprises a cannula (2020), a body (2040), and an actuation assembly (2100). Cannula (2020) includes a nitinol needle extending therethrough and is substantially the same as cannula (20) described above. In the present example, cannula (2020) and the needle are substantially identical to cannula (20) and needle (30) described above.

The primary difference between instrument (10) and instrument (2010) is that actuation assembly (2100) of instrument (2010) is rotatable instead of being slidable. Additionally, instrument (2010) includes a valve assembly (not shown) that is operable to change the fluid state of the needle. Actuation assembly (2100) is generally operable to translate the valve assembly longitudinally to thereby translate the needle longitudinally relative to cannula (2020) through rotation of a knob member (2110).

When actuation assembly (2100) is in the proximal position, an operator may rotate knob member (2110) in either a counter clockwise or clockwise direction. If knob member (2110) is rotated in the counter clockwise direction, rotation member (2110) will merely rotate freely. To begin advancement of actuation assembly (2100), the valve assembly, and the needle, an operator may rotate knob member (2110) in the clockwise direction. Clockwise rotation of knob member (2110) will act to translate knob member (2110) distally and will also act to translate the valve assembly and the needle distally. An operator may continue clockwise rotation of knob member (2110) to drive the needle out of the distal end of cannula (2020). Once the needle has been advanced to its furthest distal position relative to the distal end of cannula (2020), further clockwise rotation of knob member (2110) will merely result in free rotation of knob member (2110) due to slipping of clutch features that are integrated into actuation assembly (2100). With the needle in the distal position, the operator may actuate valve assembly to enable the delivery of therapeutic agent via the needle as described in greater detail below.

After the therapeutic agent is delivered, the operator may then wish to retract the needle. Counter clockwise rotation of knob member (2110) will cause proximal translation of actuation assembly (2100), the valve assembly, and the needle relative to body (2040). It should be understood that as actuation assembly (2100) is rotated to actuate the valve assembly, and the needle, the valve assembly and the needle remain substantially rotationally stationary relative to body (2040). It should also be understood that although rotation member (2110) of the present example is described as being manually rotated, rotation member (2110) may be rotated via a motor and/or some other motive source. Thus, it should be understood that translation of the needle may be mechanically/electrically driven via a servomotor. The actuation of a servomotor may be controlled by a servo controller as will be described in more detail below. Such a servo control may be manually operated. Additionally or alternatively, such a servo controller may be operated via a computer acting on feedback from instrument (2010) or any other component described herein.

III. Exemplary Suture Measurement Template

Figure 8:
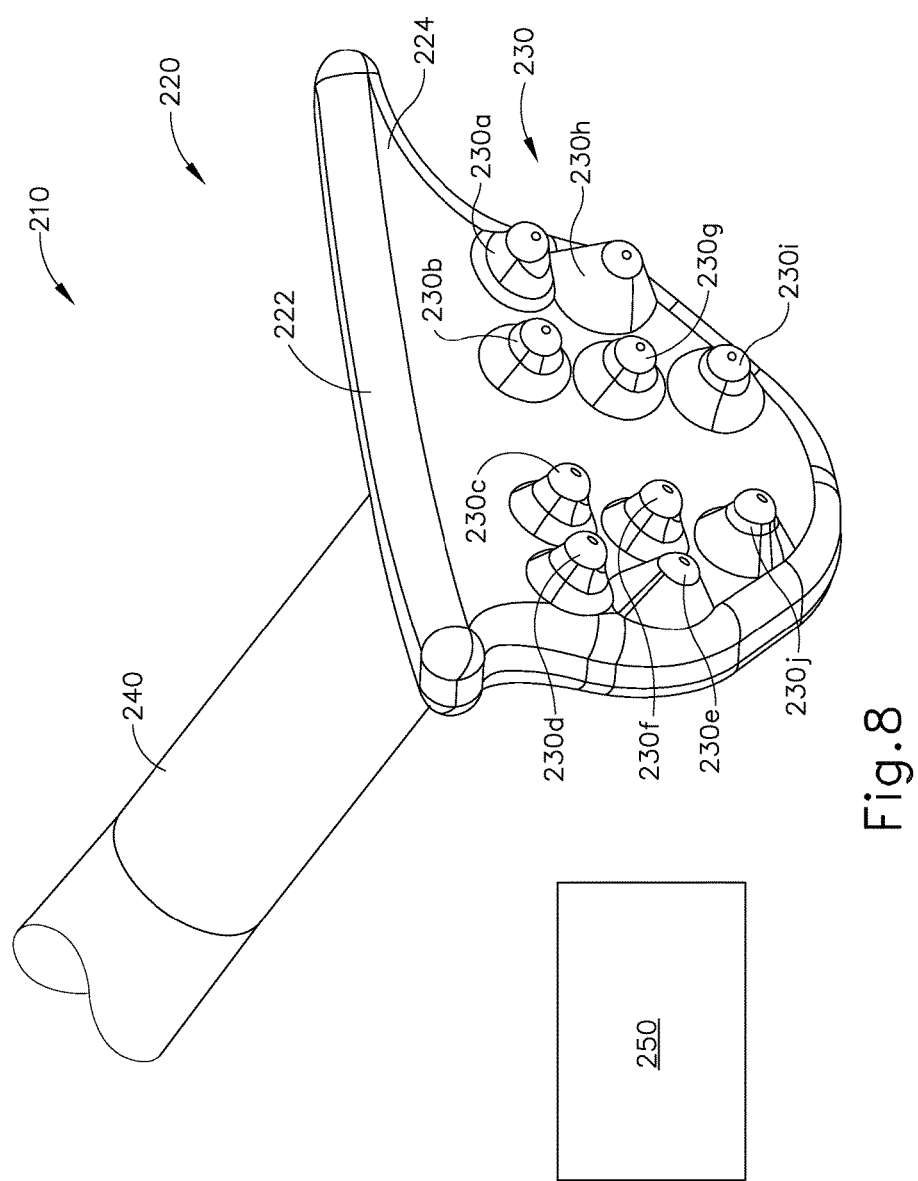
FIG. 8 depicts a perspective view of an exemplary suture measurement template for use in an exemplary method for the subretinal administration of a therapeutic agent from a suprachoroidal approach.

FIG. 8 shows an exemplary suture measurement template (210) that may be used in a procedure providing subretinal delivery of a therapeutic agent from a suprachoroidal approach, as will be described in greater detail below. Generally, template (210) is configured to be pressed against an eye of a patient to stamp a particular pattern of pigment onto the patient's eye. It should be understood that reference herein to pressing template (210) against an eye of a patent may include, but is not necessarily limited to, pressing template (210) directly against the sclera (304) surface (e.g., after the conjunctiva has been taken down or otherwise displaced). Template (210) comprises a rigid body (220) and a rigid shaft (240). As will be described in greater detail below, body (220) is generally contoured to correspond to the curvature of a patient's eye such that body (220) may be pressed or placed onto at least a portion of the patient's eye. Body (220) comprises an upper guide portion (222) and a plurality of protrusions (230) extending distally from an eye face (224) of body (220).

Upper guide portion (222) is generally semi-circular in shape and is disposed at the top of body (220). The semi-circular shape of upper guide portion (222) has a radius that corresponds to the curvature of the limbus of a patient's eye. In other words, upper guide portion (222) curves proximally along a first radius corresponding to a radius of curvature of a patient's eyeball; and downwardly (toward the longitudinal axis of shaft (240)) along a second radius corresponding to a radius of curvature of the limbus of the patient's eye. As will be described in greater detail below, upper guide portion (222) may be used to properly locate template (210) relative to the limbus of the patient's eye. Accordingly, any pigmentation that may be deposited onto a patient's eye by template may be positioned relative to the limbus of the patient's eye.

Protrusions (230) are spaced a predetermined distance from upper guide portion (222). In particular, protrusions (230) form a pattern that may correspond to relevant marks for use during the method described below. Protrusions (230) of the present example comprise four suture loop protrusions (230a-230h) and two sclerotomy protrusions (230i, 230j). Suture loop protrusions (230a-320h) and sclerotomy protrusions (230i, 230j) extend outwardly from body (220) an equal distance such that protrusions (230) collectively maintain the curvature defined by body (220). In other words, the tips of protrusions (230a-230j) all lie along a curved plane that is defined by a radius of curvature complementing the radius of curvature of the patient's eyeball. The tips of protrusions (230a-230j) are rounded and atraumatic such that protrusions (230a-230j) may be pressed against the eye without damaging the sclera or other portions of the patient's eye.

Shaft (240) extends proximally from body (220). Shaft (240) is configured to permit an operator to grasp template (210) and manipulate body (220). In the present example, shaft (240) is integral with body (220). In other examples, shaft (240) may be selectively attachable to body by a mechanical fastening means such as a threaded coupling or a mechanical snap fit, etc. In some versions, an operator may be presented with a kit comprising a shaft (240) and a plurality of bodies (220). The bodies (220) may have different curvatures to correspond with different eyeballs having different radii of curvature. The operator may thus select an appropriate body (220) from the kit based on the anatomy of the particular patient before the operator; and the operator may then secure the selected body (220) to the shaft (240). Although not shown, it should be understood that the proximal end of shaft (240) may additionally include a t-grip, knob, or other gripping feature to permit an operator to more readily grip shaft (240).

In an exemplary use, suture loop protrusions (232) and sclerotomy protrusions (234) each correspond to a particular portion of the method described below. In particular, prior to, or during the method described below, an operator may coat protrusions (230) with a biocompatible pigment or ink by pressing protrusions (230) onto a pigment or ink pad (250), by brushing the pigment or ink onto protrusions (230), or by otherwise applying the pigment or ink to protrusions (230). Once protrusions (230) have received the pigment or ink, an operator may mark an eye of a patent by pressing protrusions (230) of template (210) onto the eye of the patient, as will be described in greater detail below. Once template (210) is removed from an eye of a patient, the pigment from protrusions may remain adhered to the eye to mark particular points of interest, as will be described in greater detail below.

IV. Exemplary Method for Subretinal Delivery of Therapeutic Agent from a Suprachoroidal Approach FIGS. 9A-11C show an exemplary procedure for subretinal delivery of therapeutic agent from a suprachoroidal approach using instrument (10) described above. It should be understood however, that instrument (2010) may be readily used in addition to or in lieu of instrument (10) in the procedure described below. By way of example only, the method described herein may be employed to treat macular degeneration and/or other ocular conditions. Although the procedure described herein is discussed in the context of the treatment of age-related macular degeneration, it should be understood that no such limitation is intended or implied. For instance, in some merely exemplary alternative procedures, the same techniques described herein may be used to treat retinitis pigmentosa, diabetic retinopathy, and/or other ocular conditions. Additionally, it should be understood that the procedure described herein may be used to treat either dry or wet age-related macular degeneration.

Figure 9A:
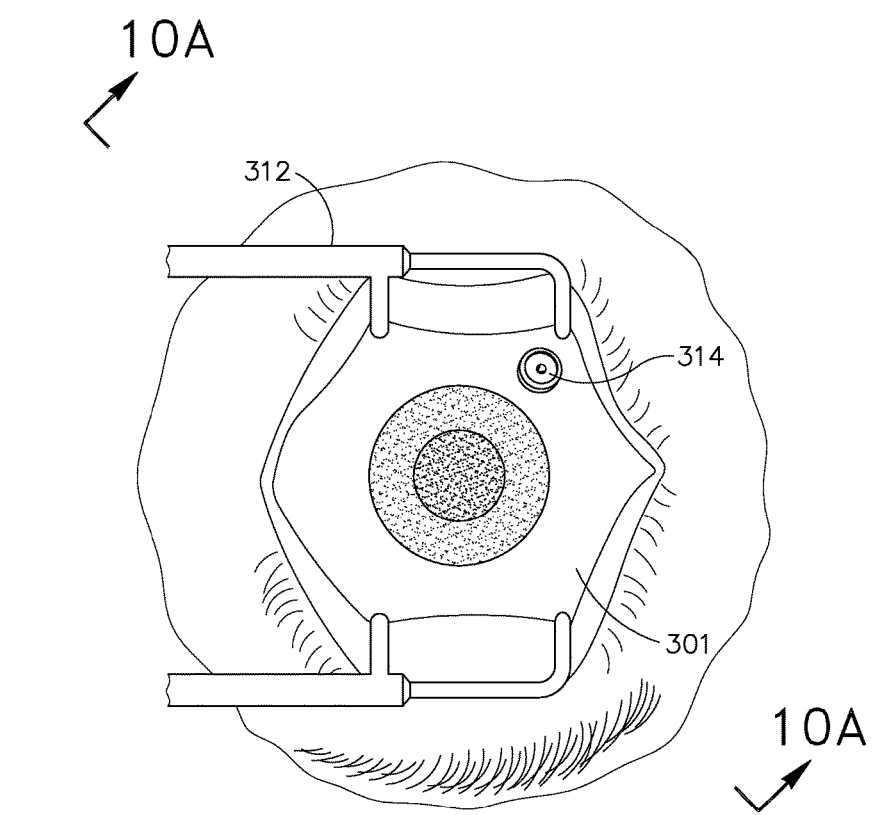
FIG. 9A depicts a top plan view of an eye of a patient, with surrounding structures of the eye immobilized and a chandelier installed.
Figure 10A:
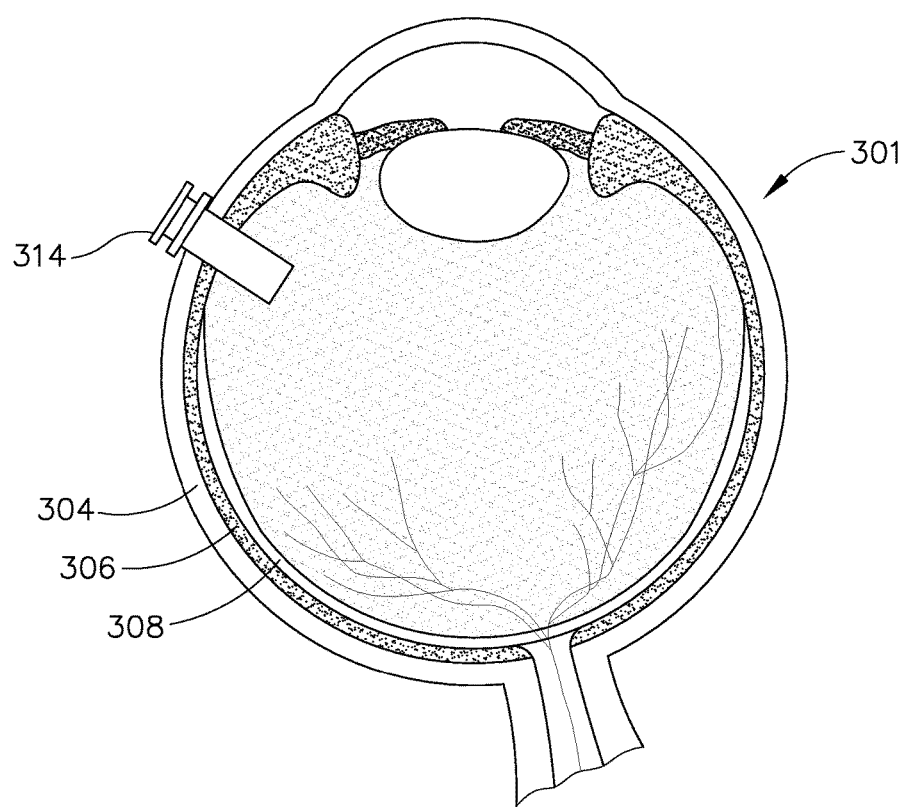
FIG. 10A depicts a cross-sectional view of the eye of FIG. 9A, with the cross-section taken about line 10A-10A of FIG. 9A.
Figure 10B:
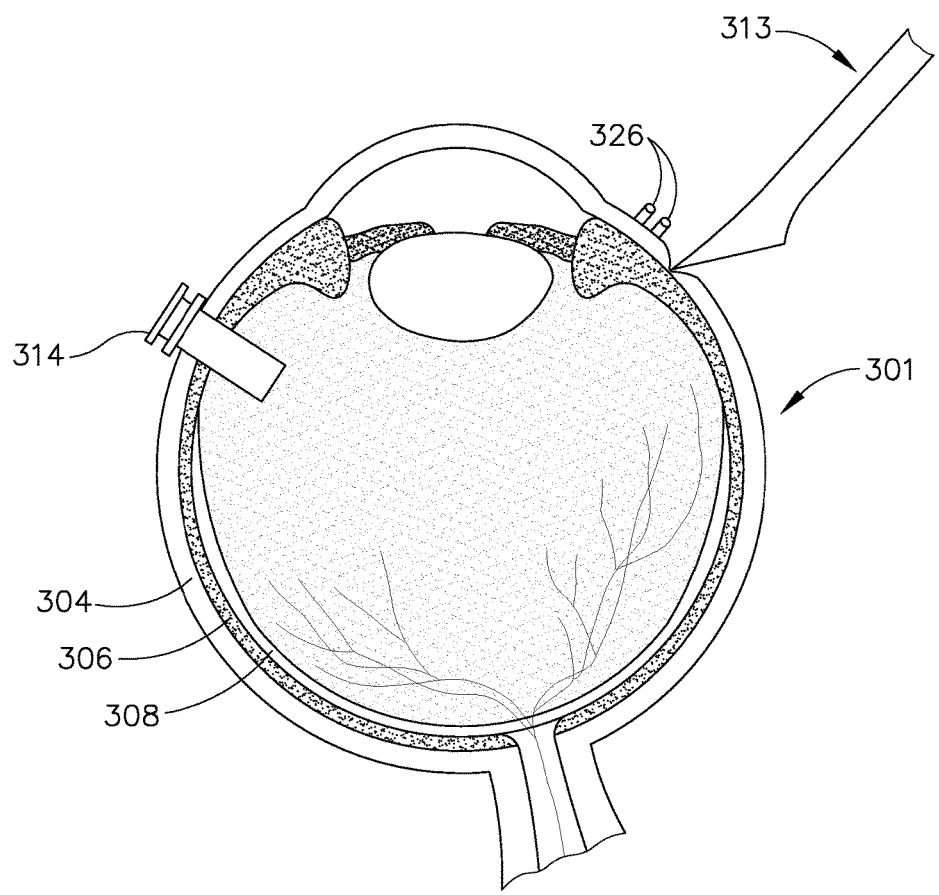
FIG. 10B depicts a cross-sectional view of the eye of FIG. 9A, with the cross-section taken about line 10B-10B of FIG. 9E.

As can be seen in FIG. 9A, the procedure begins by an operator immobilizing tissue surrounding a patient's eye (301) (e.g., the eyelids) using a speculum (312), and/or any other instrument suitable for immobilization. While is immobilization described herein with reference to tissue surrounding eye (301), it should be understood that eye (301) itself may remain free to move. Once the tissue surrounding eye (301) has been immobilized, an eye chandelier port (314) is inserted into eye (301) to provide intraocular illumination when the interior of eye (301) is viewed through the pupil. In the present example, eye chandelier port (314) is positioned in the inferior medial quadrant such that a superior temporal quadrant sclerotomy may be preformed. As can be seen in FIG. 10A, eye chandelier port (314) is positioned to direct light onto the interior of eye (314) to illuminate at least a portion of the retina (e.g., including at least a portion of the macula). As will be understood, such illumination corresponds to an area of eye (301) that is being targeted for delivery of therapeutic agent. In the present example, only chandelier port (314) is inserted at this stage, without yet inserting an optical fiber (315) into port (314). In some other versions, an optical fiber (315) may be inserted into chandelier port (314) at this stage. In either case, a microscope may optionally be utilized to visually inspect the eye to confirm proper positioning of eye chandelier port (314) relative to the target site. In some examples, the target region may be identified by a relative lack of retinal pigmentation. Although FIG. 9A shows a particular positioning of eye chandelier port (314), it should be understood that eye chandelier port (314) may have any other positioning as will be apparent to those of ordinary skill in the art in view of the teachings herein.

Figure 9B:
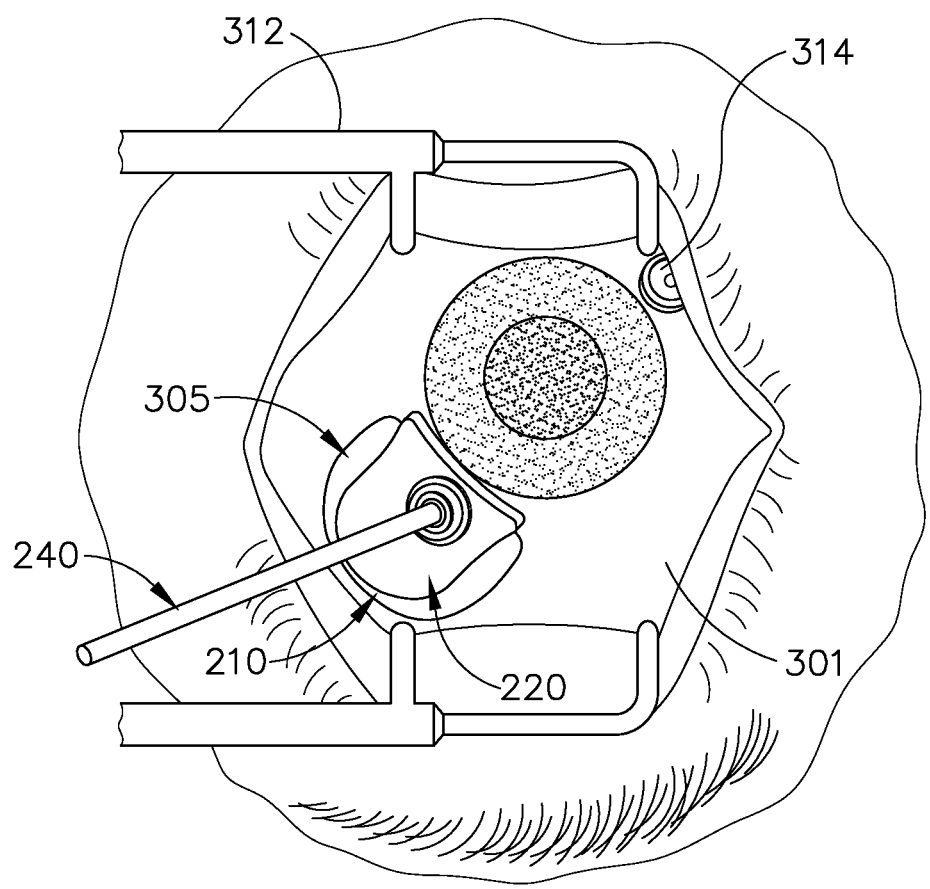
FIG. 9B depicts a top plan view of the eye of FIG. 9A, with the template of FIG. 8 disposed on the eye.
Figure 9C:
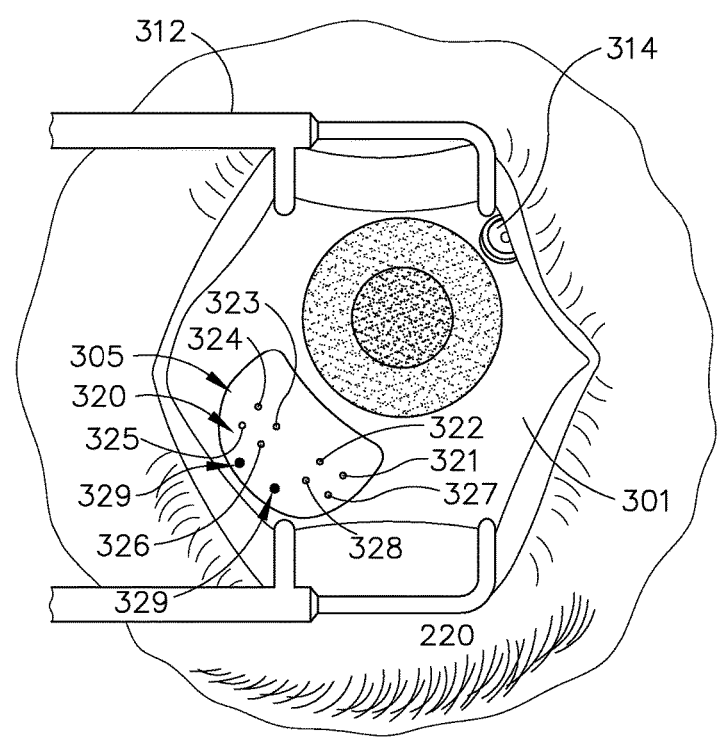
FIG. 9C depicts a top plan view of the eye of FIG. 9A, with a plurality of markers disposed on the eye.

Once eye chandelier port (314) has been positioned, the sclera (304) may be accessed by dissecting the conjunctiva by incising a flap in the conjunctiva and pulling the flap posteriorly. After such a dissection is completed, the exposed surface (305) of the sclera (304) may optionally be blanched using a cautery tool to minimize bleeding. Once conjunctiva dissection is complete, the exposed surface (305) of the sclera (304) may optionally be dried using a WECK-CEL or other suitable absorbent device. Template (210), described above, may then be used to mark eye (301). As can be seen in FIG. 9B, template (210) is positioned to align with the limbus of eye (301). An operator may apply a light force to template (210) to apply pigment to eye (301). Template (210) is then removed, leaving pigment adhered to the exposed surface (305) of the sclera (304) to provide a visual guide (320) for an operator, as can be seen in FIG. 9C. An operator may then use visual guide (320) to attach a suture loop assembly (330) and to perform a sclerotomy.

Visual guide (320) comprises a set of suture loop markers (321, 322, 323, 324, 325, 326, 327) and a pair of sclerotomy markers (329).

Figure 9D:
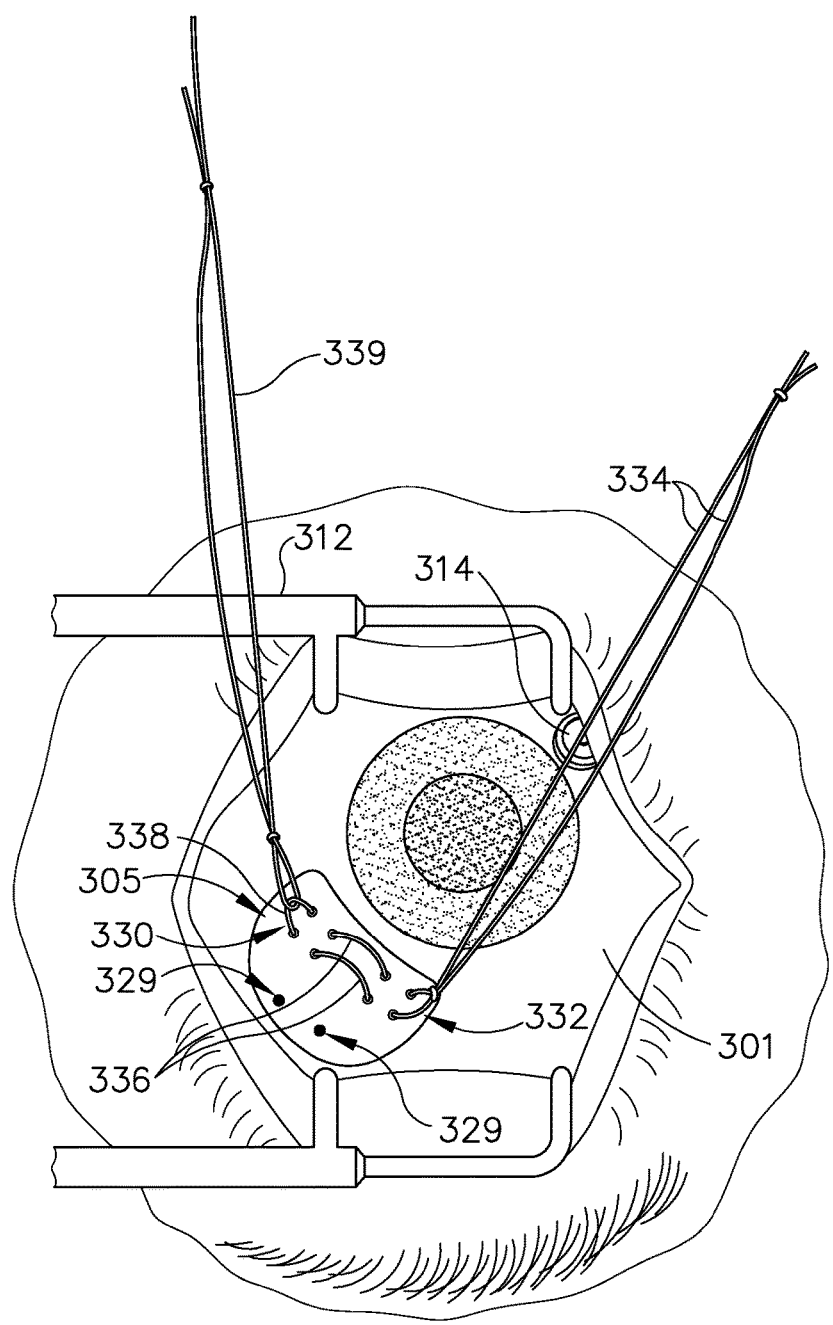
FIG. 9D depicts a top plan view of the eye of FIG. 9A, with a suture loop attached to the eye.
Figure 9E:
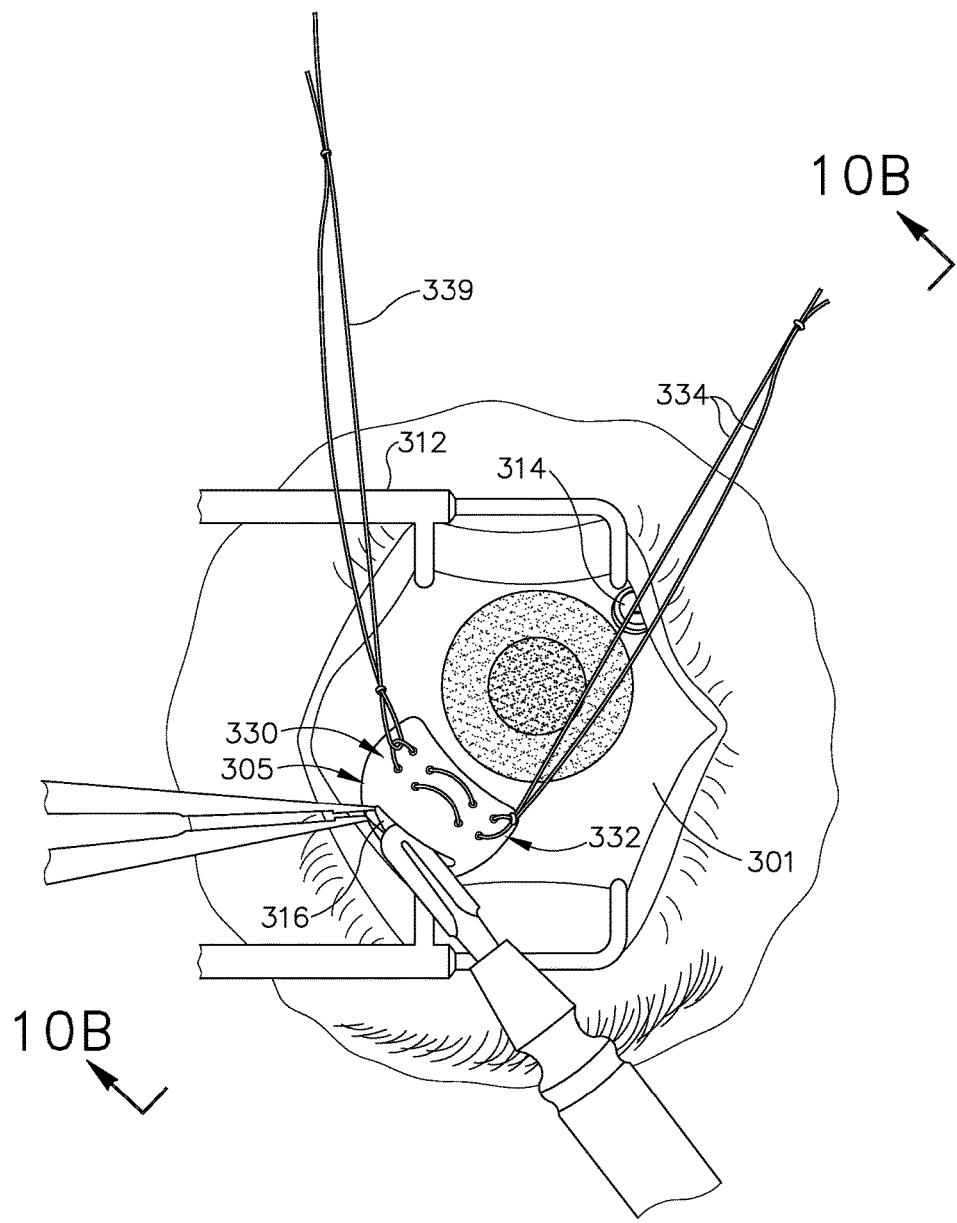
FIG. 9E depicts a top plan view of the eye of FIG. 9A, with a sclerotomy being performed.

FIG. 9D shows a completed suture loop assembly (330). As will be described in greater detail below, suture loop assembly (330) is generally configured to guide cannula (20) of instrument (10) through a sclerotomy and into eye (301). An exemplary procedure that may be employed to create the suture loop assembly (330) that is shown in FIG. 9D is described in U.S. patent application Ser. No. 14/619,256, entitled "Method and Apparatus for Suprachoroidal Administration of Therapeutic Agent," filed Feb. 11, 2015, the disclosure of which is incorporated by reference herein. Once suture loop assembly (330) has been attached to eye (301), a sclerotomy may be performed on eye (301). As seen in FIG. 9E, eye (301) is cut between sclerotomy markers (329) using a conventional scalpel (313) or other suitable cutting instrument. Although sclerotomy markers (329) are shown as comprising two discrete dots, it should be understood that in other examples, markers (329) may comprise any other type of markings such as a solid, dotted or dashed line. The sclerotomy procedure forms a small incision (316) through sclera (304) of eye (301). As can best be seen in FIG. 10B, the sclerotomy is preformed with particular care to avoid penetration of the choroid (306). Thus, the sclerotomy procedure provides access to the space between sclera (304) and choroid (306). Once incision (316) is made in eye (301), a blunt dissection may optionally be performed to locally separate sclera (304) from choroid (306). Such a dissection may be performed using a small blunt elongate instrument, as will be apparent to those of ordinary skill in the art in view of the teachings herein.

Figure 9F:
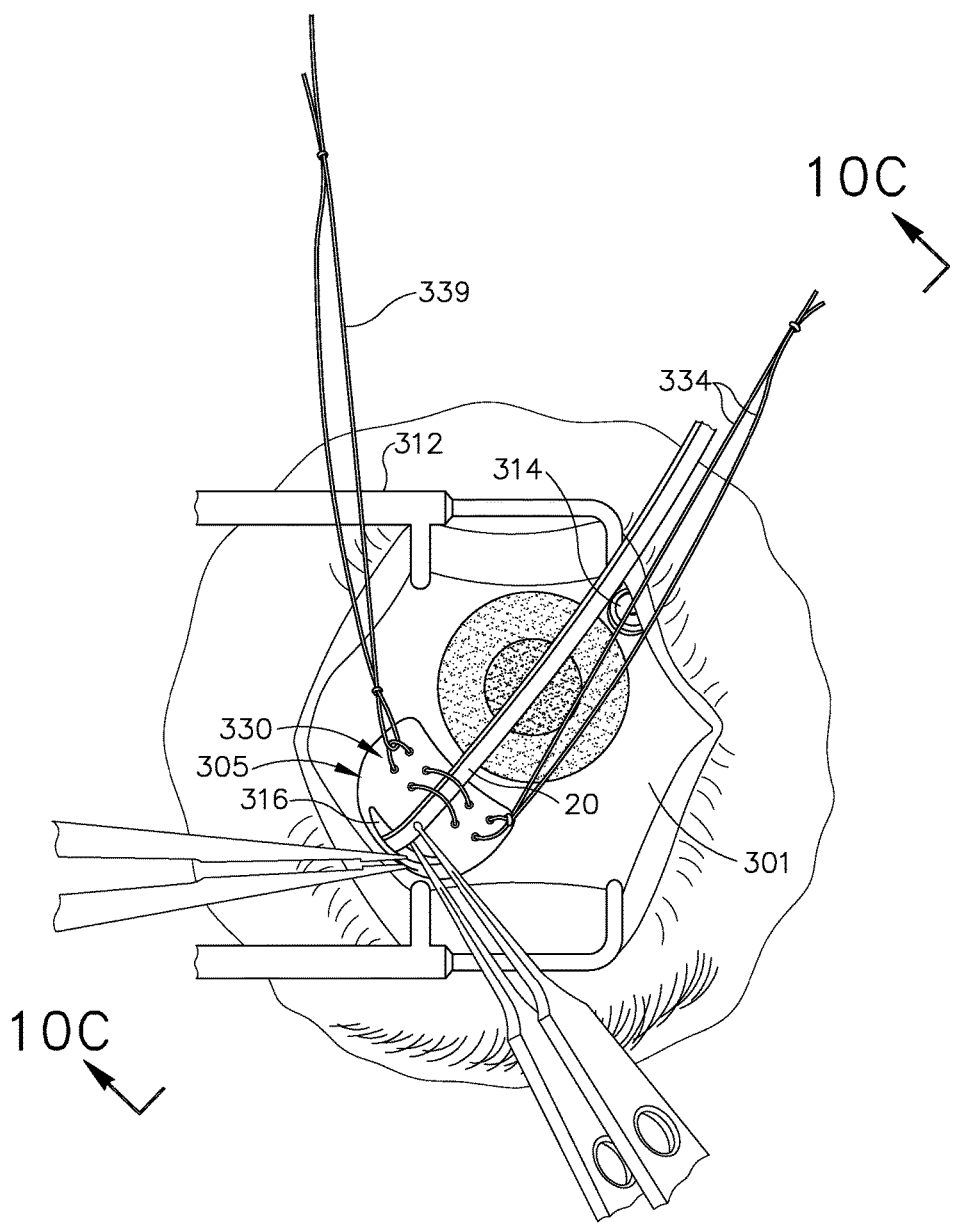
FIG. 9F depicts a top plan view of the eye of FIG. 9A, with the instrument of FIG. 1 being inserted through the sclerotomy opening and in between the sclera and choroid of the eye.

With the sclerotomy procedure performed, an operator may insert cannula (20) of instrument (10) through incision (316) and into the space between sclera (304) and choroid (306). As can be seen in FIG. 9F, cannula (20) is directed through guide loops (336) of suture loop assembly (330) and into incision (316). As described above, guide loops (336) may stabilize cannula (20). Additionally, guide loops (336) maintain cannula (20) in a generally tangential orientation relative to incision (316). Such tangential orientation may reduce trauma as cannula (20) is guided through incision (316) to stabilize cannula (20) and to prevent damage to surrounding tissue. As cannula (20) is inserted into incision (316) through guide loops (336), an operator may use forceps or other instruments to further guide cannula (20) along an atraumatic path. Of course, use of forceps or other instruments is merely optional, and may be omitted in some examples. Although not shown, it should be understood that in some examples cannula (20) may include one or more markers on the surface of cannula (20) to indicate various depths of insertion. While merely optional, such markers may be desirable to aid an operator in identifying the proper depth of insertion as cannula (20) is guided along an atraumatic path. For instance, the operator may visually observe the position of such markers in relation to guide loops (336) and/or in relation to incision (316) as an indication of the depth to which cannula (20) is inserted in eye (301). By way of example only, one such marker may correspond to an approximately 6 mm depth of insertion of cannula (20).

Once cannula (20) is at least partially inserted into eye (301), an operator may insert an optical fiber (315) into eye chandelier port (314) if the fiber (315) had not yet been inserted at this stage. With eye chandelier port (314) in place and assembled with optical fiber (315), an operator may activate eye chandelier port (314) by directing light through optical fiber (315) to provide illumination of eye (301) and thereby visualize the interior of eye (301). Further adjustments to the positioning of cannula (20) may optionally be made at this point to ensure proper positioning relative to the area of geographic atrophy of retina (308). In some instances, the operator may wish to rotate the eye (301), such as by pulling on sutures (334, 339), to direct the pupil of the eye (301) toward the operator in order to optimize visualization of the interior of the eye (301) via the pupil.

Figure 9G:
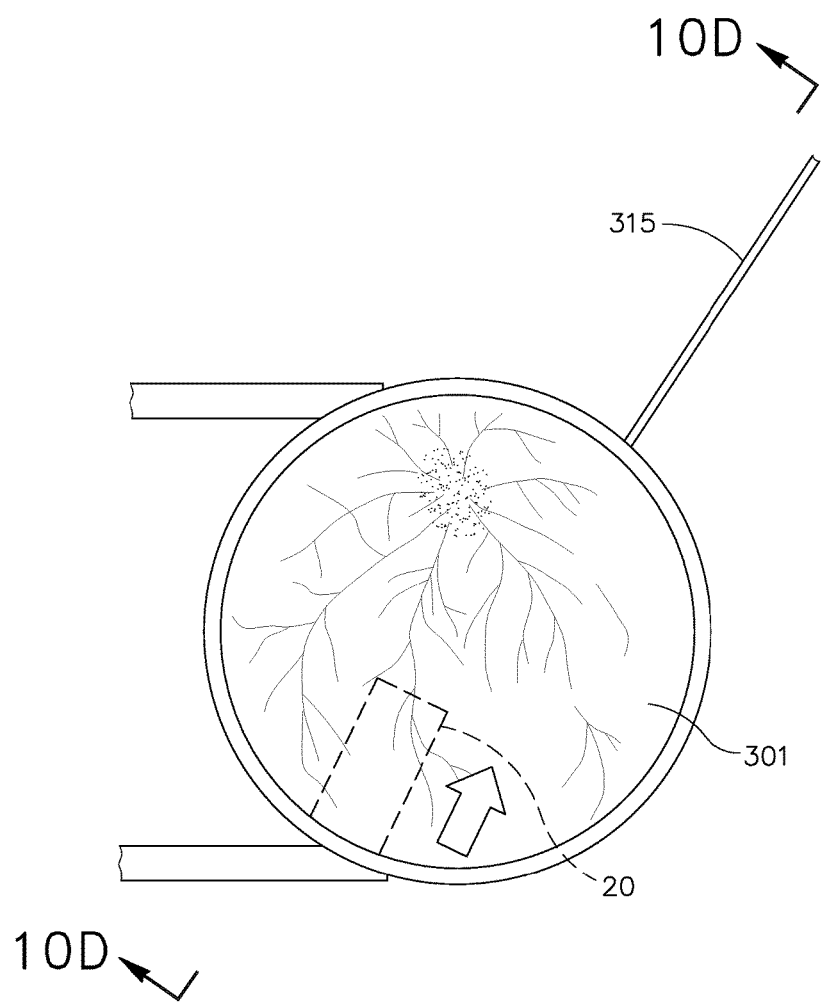
FIG. 9G depicts a top plan view of the eye of FIG. 9A, with the instrument of FIG. 1 under direct visualization at the back of the eye, between the sclera and choroid.
Figure 10C:
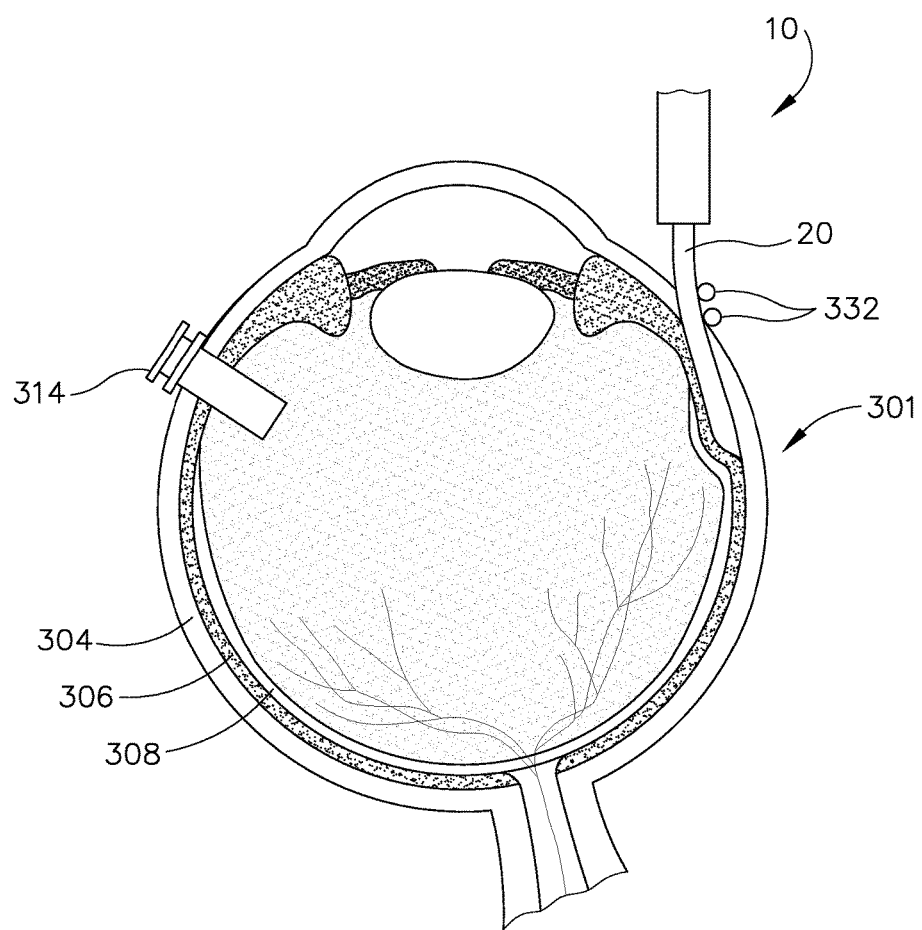
FIG. 10C depicts a cross-sectional view of the eye of FIG. 9A, with the cross-section taken about line 10C-10C of FIG. 9F.
Figure 10D:
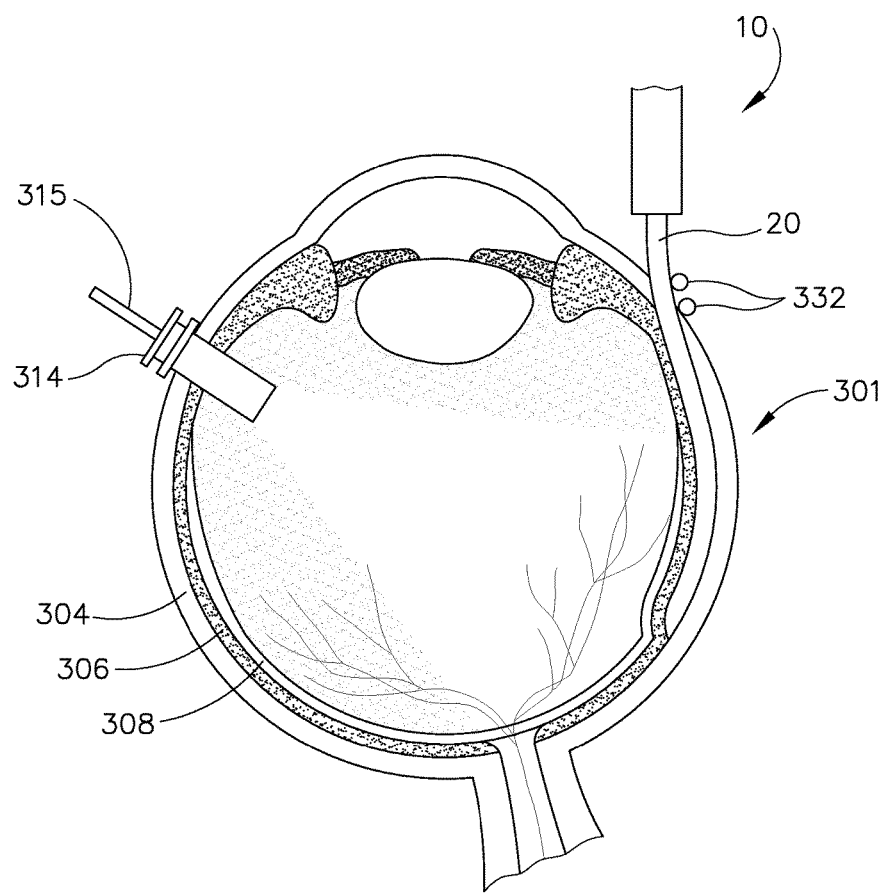
FIG. 10D depicts a cross-sectional view of the eye of FIG. 9A, with the cross-section taken about line 10D-10D of FIG. 9G.
Figure 10E:
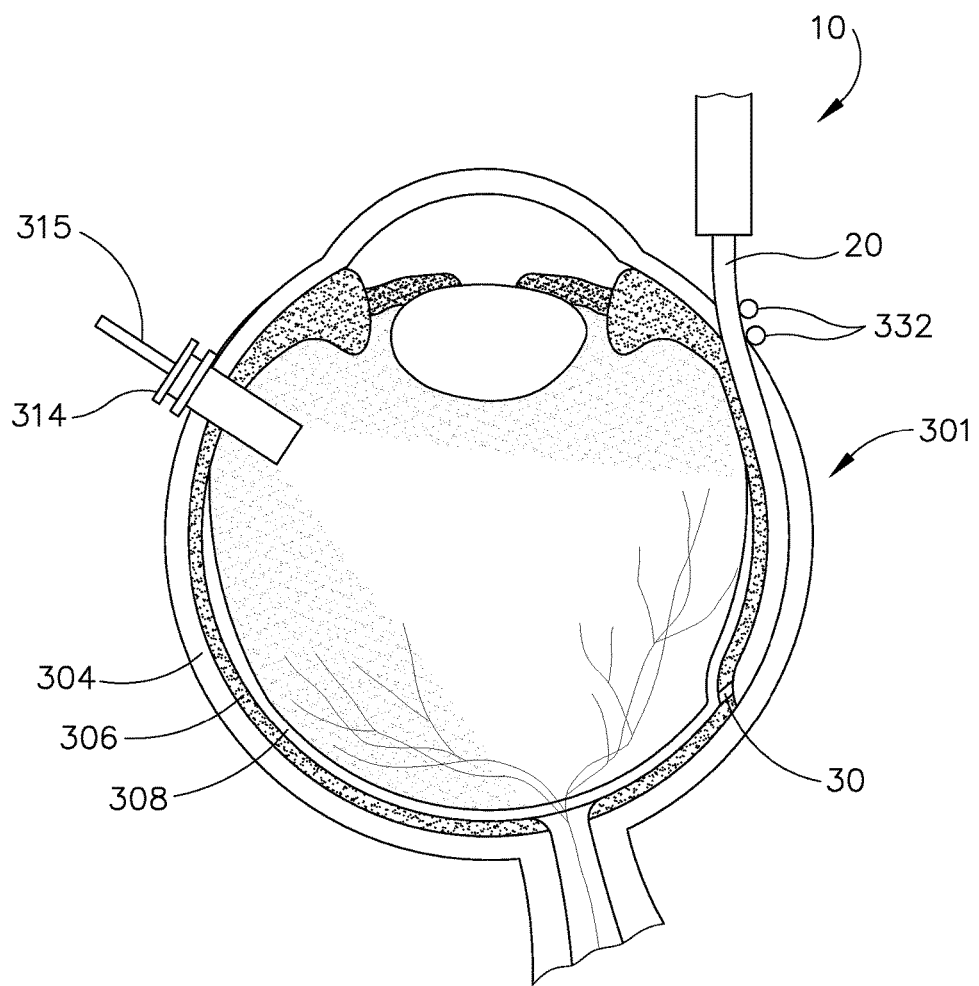
FIG. 10E depicts a cross-sectional view of the eye of FIG. 9A, with the cross-section taken about line 10E-10E of FIG. 9H.

FIGS. 9G and 10C-10D show cannula (20) as it is guided between sclera (304) and choroid (306) to the delivery site for the therapeutic agent. In the present example, the delivery site corresponds to a generally posterior region of eye (301) adjacent to an area of geographic atrophy of retina (308). In particular, the delivery site of the present example is superior to the macula, in the potential space between the neurosensory retina and the retinal pigment epithelium layer. FIG. 9G shows eye (301) under direct visualization through a microscope directed through the pupil of eye (301), with illumination provided through fiber (315) and port (314). As can be seen, cannula (20) is at least partially visible through a retina (308) and choroid (306) of eye (301). Thus, an operator may track cannula (20) as it is advanced through eye (301) from the position shown in FIG. 10C to the position shown in 10D. Such tracking may be enhanced in versions where an optical fiber (34) is used to emit visible light through the distal end of cannula (20).

Figure 9H:
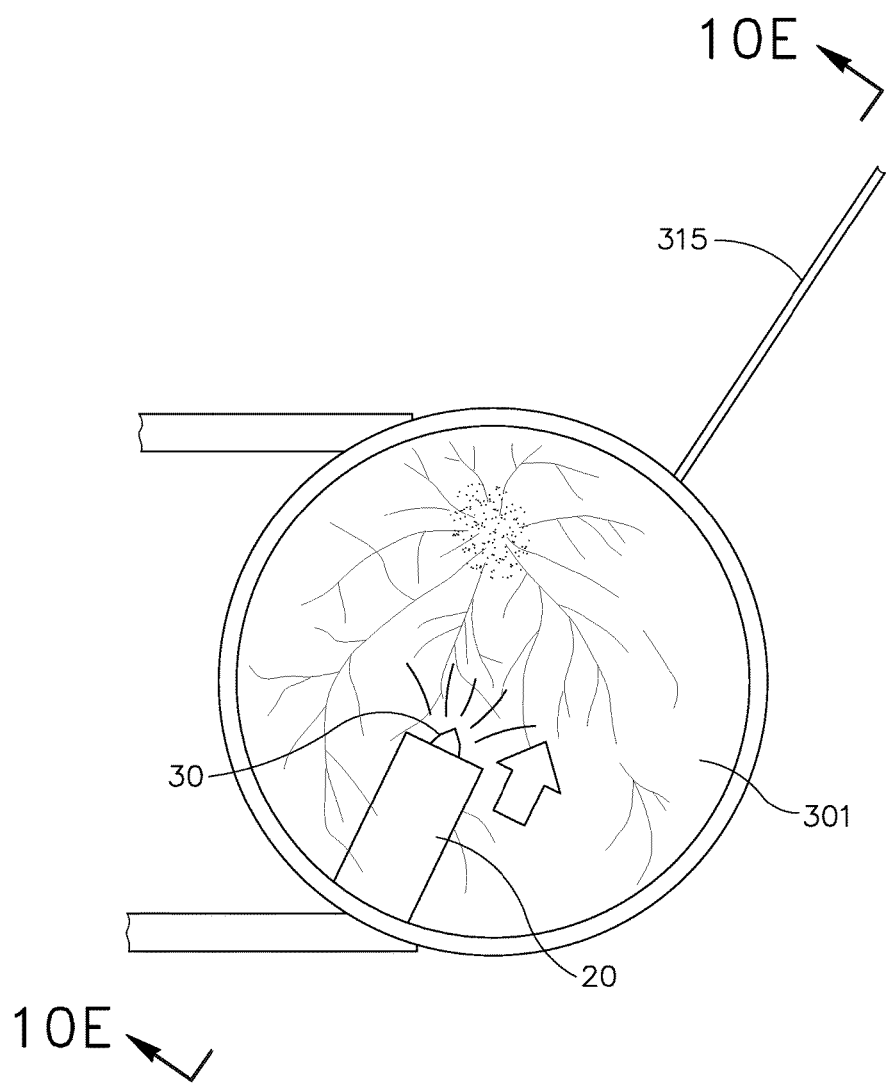
FIG. 9H depicts a top plan view of the eye of FIG. 9A, with the needle of the instrument of FIG. 1 being advanced under direct visualization at the back of the eye, pressing against the outer surface of the choroid causing the choroid to 'tent'.

Once cannula (20) has been advanced to the delivery site as shown in FIG. 10D, an operator may advance needle (30) of instrument (10) as described above with respect to FIGS. 3-4. As can be seen in FIGS. 9H-9I, 10E, and 11A, needle (30) is advanced relative to cannula (20) such that needle (30) pierces through choroid (306) without penetrating retina (308). Immediately prior to penetrating choroid (306), needle (30) may appear under direct visualization as "tenting" the surface of choroid (306), as can be seen in FIG. 9H. In other words, needle (30) may deform choroid (306) by pushing upwardly on choroid, providing an appearance similar to a tent pole deforming the roof of a tent. Such a visual phenomenon may be used by an operator to identify whether choroid (306) is about to be pierced and the location of any eventual piercing. The particular amount of needle (30) advancement sufficient to initiate "tenting" and subsequent piercing of choroid (306) may be of any suitable amount as may be determined by a number of factors such as, but not limited to, general patient anatomy, local patient anatomy, operator preference, and/or other factors. As described above, a merely exemplary range of needle (30) advancement may be between approximately 0.25 mm and approximately 10 mm; or more particularly between approximately 2 mm and approximately 6 mm.

Figure 9I:
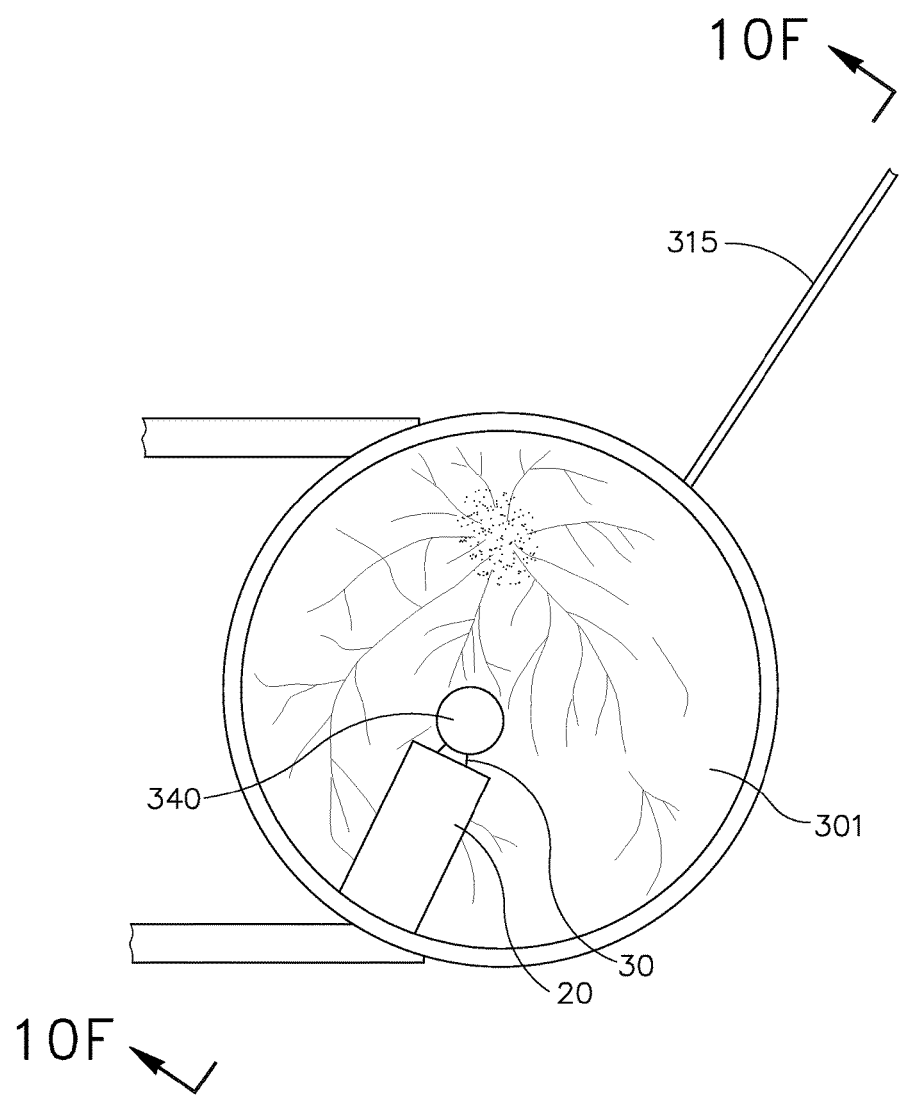
FIG. 9I depicts a top plan view of the eye of FIG. 9A, with the needle dispensing a leading bleb under direct visualization at the back of the eye, the needle between the sclera and choroid, and the leading bleb in the sub retinal space between the choroid and a retina.
Figure 10F:
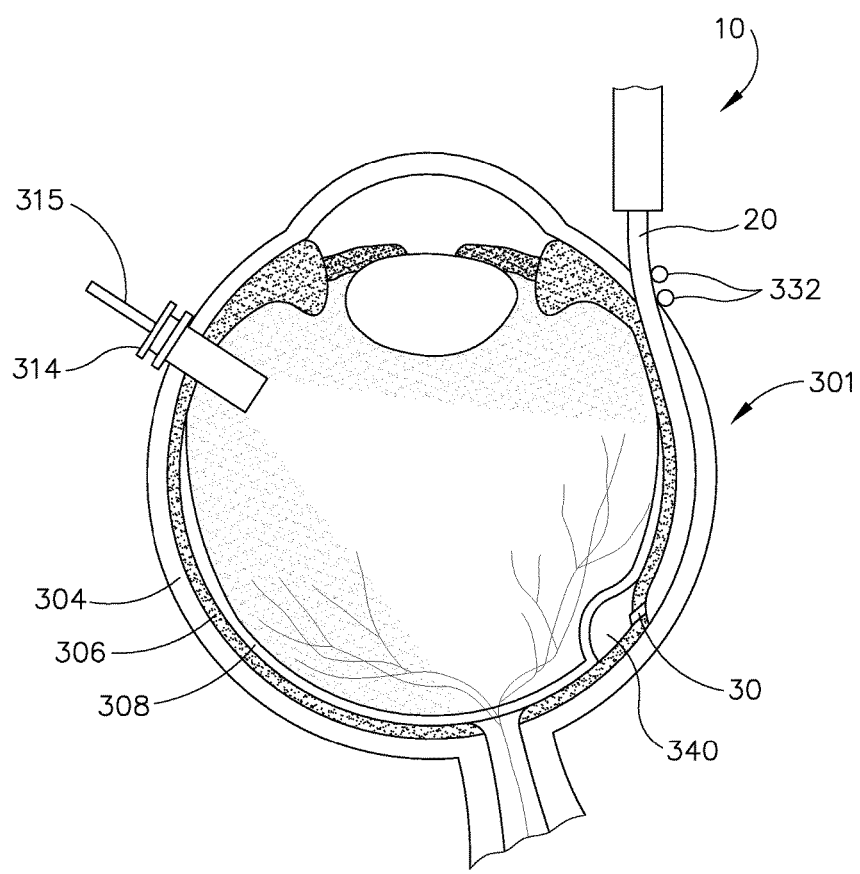
FIG. 10F depicts a cross-sectional view of the eye of FIG. 9A, with the cross-section taken about line 10F-10F of FIG. 9I.
Figure 11A:
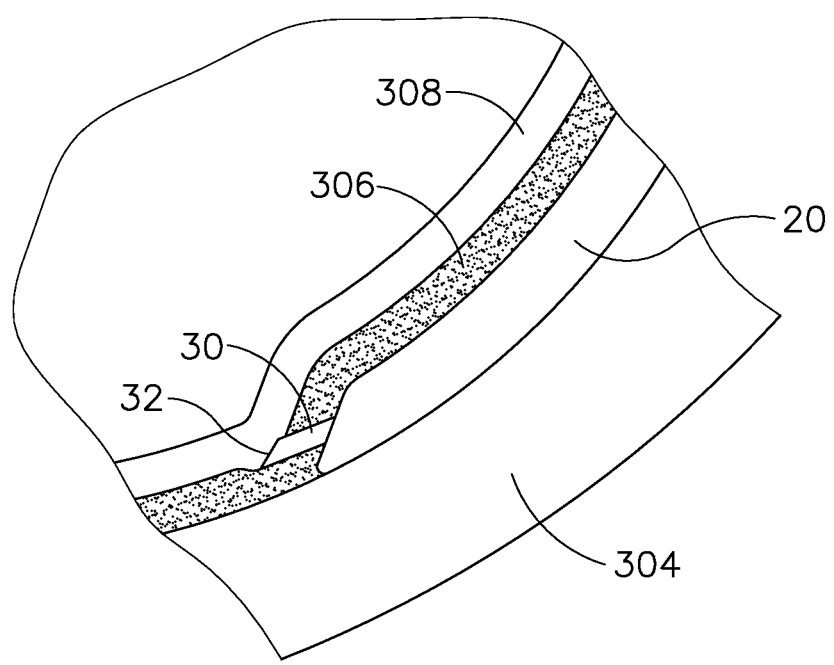
FIG. 11A depicts a detailed cross-sectional view of the eye of FIG. 9A depicted in the state shown in FIG. 10E.
Figure 11B:
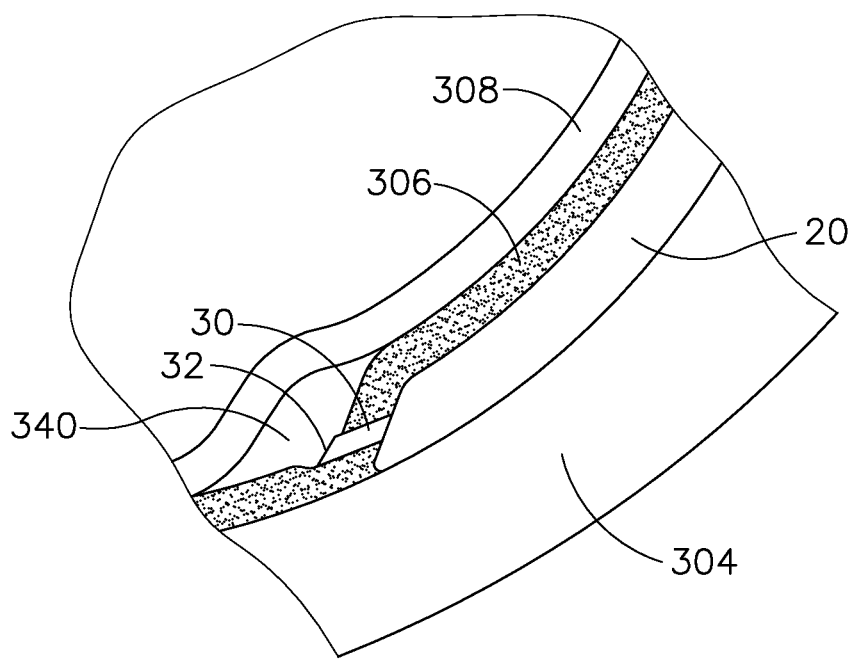
FIG. 11B depicts a detailed cross-sectional view of the eye of FIG. 9A depicted in the state shown in FIG. 10F.

In the present example, after the operator has confirmed that needle (30) has been properly advanced by visualizing the tenting effect described above, the operator infuses a balanced salt solution (BSS) or other similar solution as needle (30) is advanced relative to cannula (20). Such a BSS solution may form a leading bleb (340) ahead of needle (30) as needle (30) is advanced through choroid (306). Leading bleb (340) may be desirable for two reasons. First, as shown in FIGS. 9I, 10F, and 11B, leading bleb (340) may provide a further visual indicator to an operator to indicate when needle (30) is properly positioned at the delivery site. Second, leading bleb (340) may provide a barrier between needle (30) and retina (308) once needle (30) has penetrated choroid (306). Such a barrier may push the retinal wall outwardly (as is best seen in FIGS. 10F and 11B), thereby minimizing the risk of retinal perforation as needle (30) is advanced to the delivery site. In some versions, a foot pedal is actuated in order to drive leading bleb (340) out from needle (30). Alternatively, other suitable features that may be used to drive leading bleb (340) out from needle (30) will be apparent to those of ordinary skill in the art in view of the teachings herein.

Once the operator visualizes leading bleb (340), the operator may cease infusion of BSS, leaving a pocket of fluid as can be seen in FIGS. 9I, 10F, and 11B. Next, a therapeutic agent (341) may be infused by actuating a syringe or other fluid delivery device as described above with respect to instrument (10). The particular therapeutic agent (341) delivered may be any suitable therapeutic agent configured to treat an ocular condition. Some merely exemplary suitable therapeutic agents may include, but are not necessarily limited to, drugs having smaller or large molecules, therapeutic cell solutions, certain gene therapy solutions, and/or any other suitable therapeutic agent as will be apparent to those of ordinary skill in the art in view of the teachings herein. By way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein.

Figure 9J:
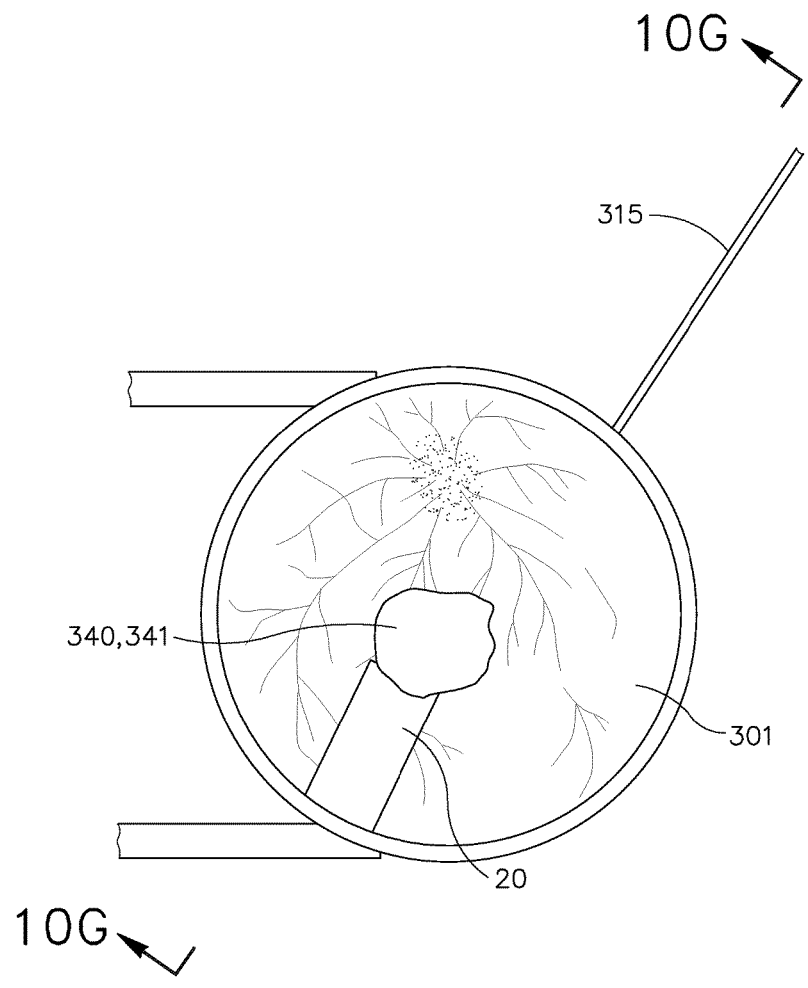
FIG. 9J depicts a top plan view of the eye of FIG. 9A, with the needle dispensing a therapeutic agent to the eye at the back of the eye, between the sclera and choroid.
Figure 10G:
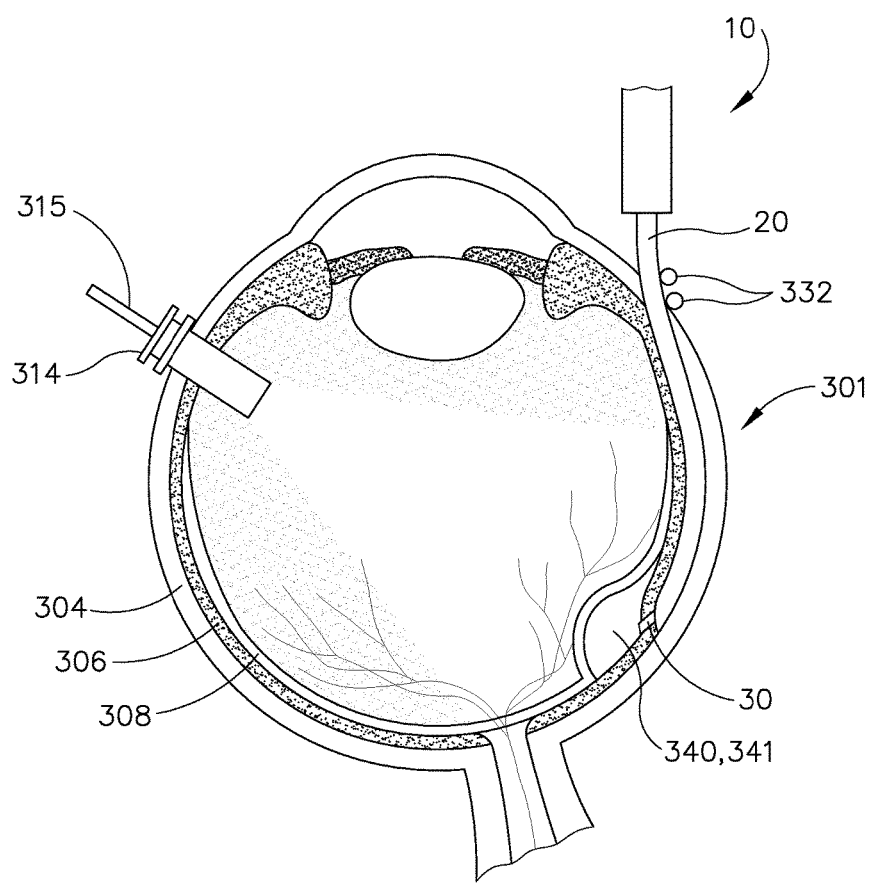
FIG. 10G depicts a cross-sectional view of the eye of FIG. 9A, with the cross-section taken about line 10G-10G of FIG. 9J.
Figure 11C:
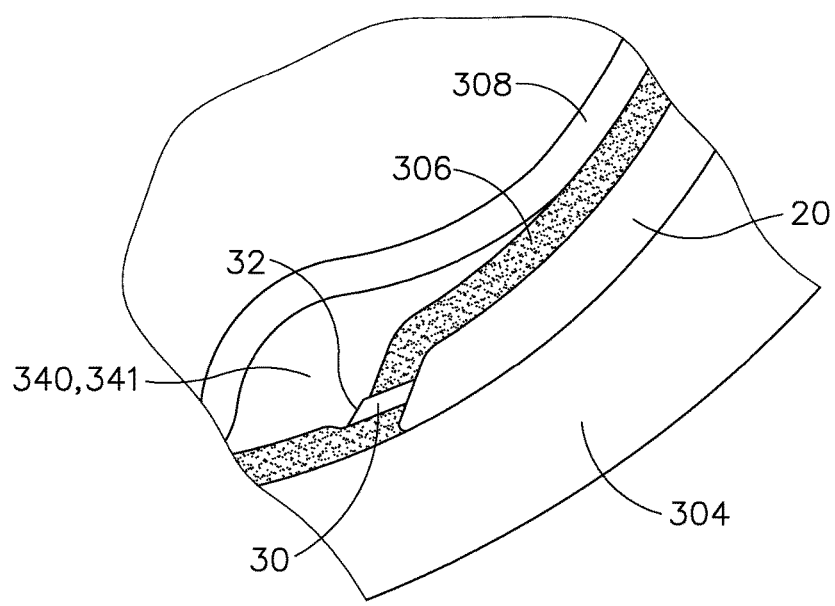
FIG. 11C depicts a detailed cross-sectional view of the eye of FIG. 9A depicted in the state shown in FIG. 10G.

In the present example, the amount of therapeutic agent (341) that is ultimately delivered to the delivery site is approximately 50 µL, although any other suitable amount may be delivered. In some versions, a foot pedal is actuated in order to drive agent (341) out from needle (30). Alternatively, other suitable features that may be used to drive agent (341) out from needle (30) will be apparent to those of ordinary skill in the art in view of the teachings herein. Delivery of therapeutic agent may be visualized by an expansion of the pocket of fluid as can be seen in FIGS. 9J, 10G, and 11C. As shown, therapeutic agent (341) essentially mixes with the fluid of leading bleb (340) as therapeutic agent (341) is injected into the surprachoroidal space.

Once delivery is complete, needle (20) may be retracted by sliding actuation assembly (60) proximally relative to body (40); and cannula (30) may then be withdrawn from eye (301). It should be understood that because of the size of needle (20), the site where needle (20) penetrated through choroid (306) is self sealing, such that no further steps need be taken to seal the delivery site through choroid (306). Suture loop assembly (330) and chandelier (314) may be removed, and incision (316) in the sclera (304) may be closed using any suitable conventional techniques.

As noted above, the foregoing procedure may be carried out to treat a patient having macular degeneration. In some such instances, the therapeutic agent (341) that is delivered by needle (20) may comprise cells that are derived from postpartum umbilicus and placenta. As noted above, and by way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. Alternatively, needle (20) may be used to deliver any other suitable substance or substances, in addition to or in lieu of those described in U.S. Pat. No. 7,413,734 and/or elsewhere herein. By way of example only, therapeutic agent (341) may comprise various kinds of drugs including but not limited to small molecules, large molecules, cells, and/or gene therapies. It should also be understood that macular degeneration is just one merely illustrative example of a condition that may be treated through the procedure described herein. Other biological conditions that may be addressed using the instruments and procedures described herein will be apparent to those of ordinary skill in the art.

V. Exemplary Therapeutic Agent Delivery Instrument with Motorized Articulation Feature In some instances, it might be beneficial to automate the motion of needle (30) into and out of the suprachoroidal space of the eye during a procedure for the subretinal administration of a therapeutic agent from a suprachoroidal approach to an eye of a patient. Motorization may reduce risks that might otherwise be associated with operator error of manually actuated instruments such as instruments (10, 2010). In particular, after cannula (20) is inserted into position at the injection site as described above, it may be desirable to advance needle (30) forward via an automated actuation assembly (405) controlled by activation button (411). Motorized needle (30) advancement may be optimized for smooth choroidal penetration and minimal tenting of the choroid during needle (30) advancement. Additionally, motorized needle (30) advancement may allow for enhanced control of needle (30) motion parameters such as speed, vibration, oscillation, rotation, and jackhammering.

FIGS. 12-17B show an exemplary motorized instrument (400) that is configured for use in a procedure for the subretinal administration of a therapeutic agent from a suprachoroidal approach to an eye of a patient. Similar to instrument (10) described above, motorized exemplary instrument (400) comprises flexible cannula (4200), needle (4300), cannula attachment member (42), and a body (410). As mentioned above, flexible cannula (4200) is attached to the distal end of body (410) by cannula attachment member (42), and needle (4300) is slidably disposed within flexible cannula (4200). It should be understood that cannula (4200) of instrument (400) in this example is identical to cannula (20) of instrument (10) described above. Similarly, needle (4300) of instrument (400) in this example is identical to needle (30) of instrument (10) described above.

Figure 12:
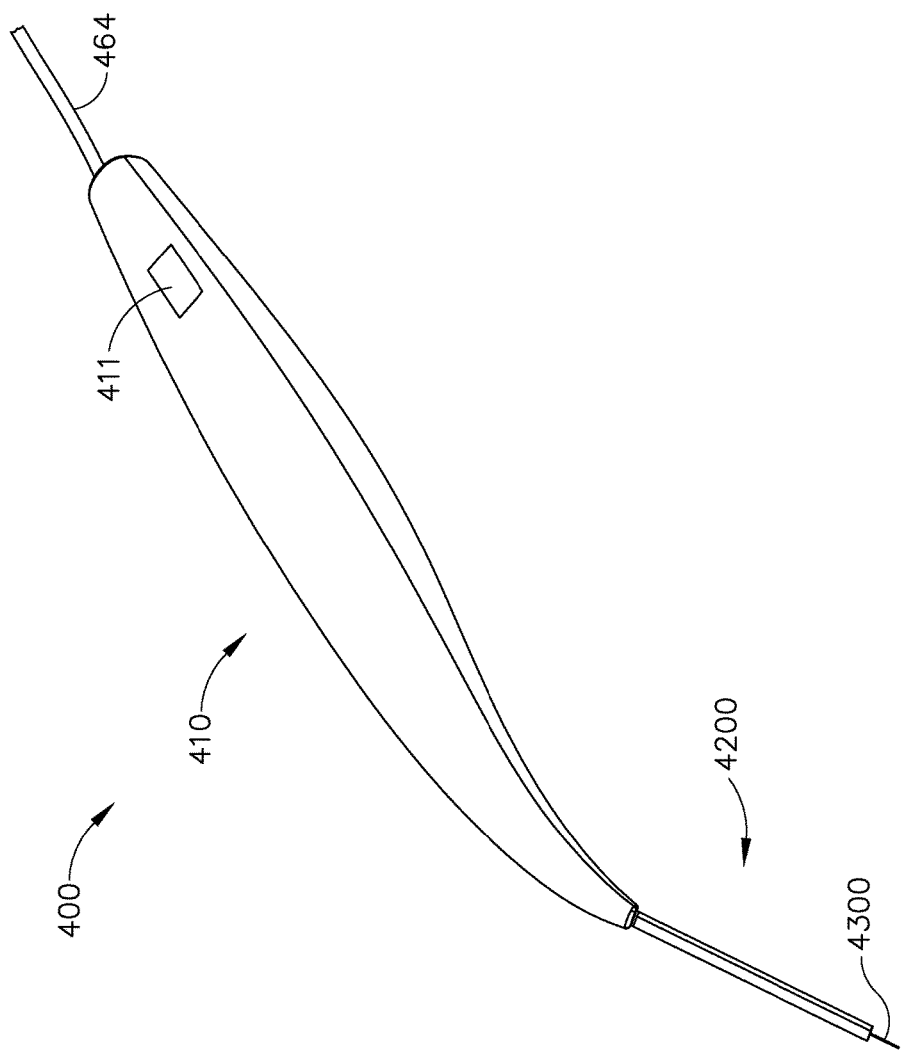
FIG. 12 depicts a perspective view of an exemplary alternative instrument that may be used to provide subretinal administration of a therapeutic agent from a suprachoroidal approach.

As shown in FIG. 12, instrument (400) of this example further comprises activation button (411) located on body (411). Activation button (411) is configured to activate a motor (420) (shown in FIGS. 13-17B), eventually leading to actuation of needle (4300). Of course, activation button (411) does not have to be located on body, but could be separate from body and may comprise a foot pedal, a hand switch, or any other form known to a person having ordinary skill in the art in view of the teachings herein. In some examples, motor (420) receives electrical power from a source within body (411), such as a battery (not shown). In some other examples, motor (420) receives electrical power from a source external to body (411). For instance, wires may couple motor (420) with a conventional wall outlet or a piece of capital equipment that is operable to provide electrical power. Other devices and techniques that may be used to provide electrical power to motor (420) will apparent to a personal having ordinary skill in the art in view of the teachings herein.

Figure 13:
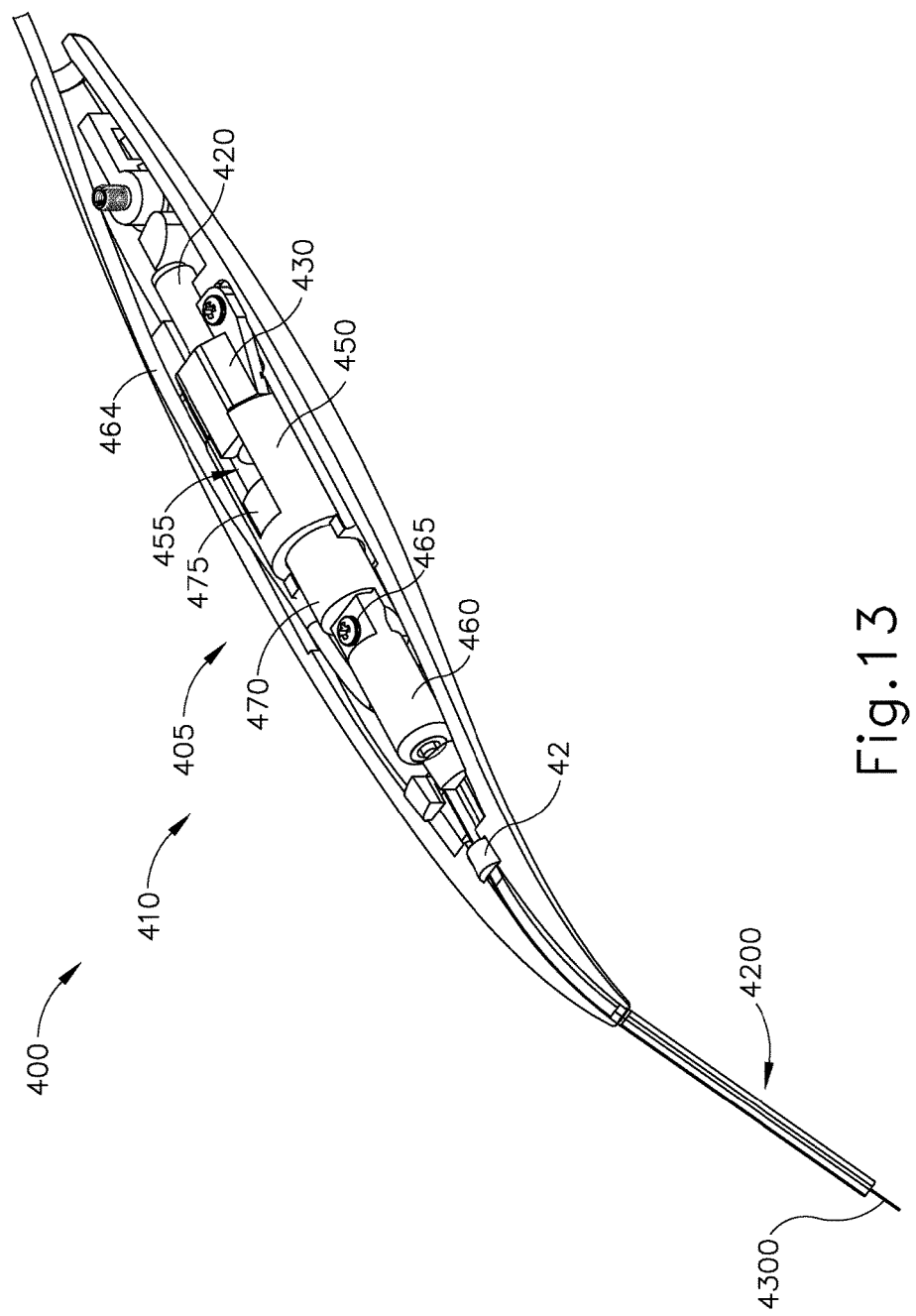
FIG. 13 depicts a perspective view of the instrument of FIG. 12, with a top portion of the body omitted.
Figure 14:
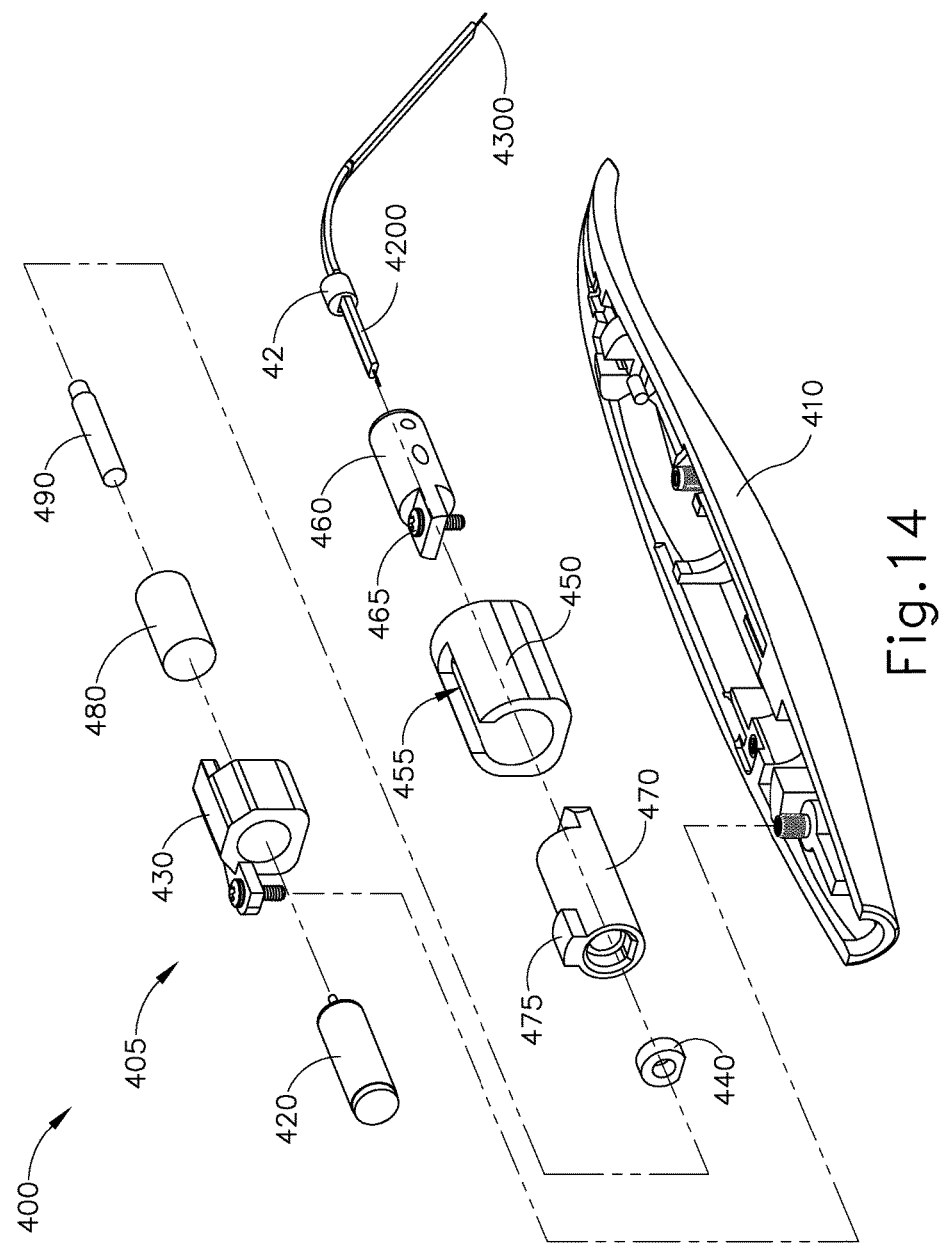
FIG. 14 depicts an exploded perspective view of the instrument of FIG. 12, with a top portion of the body omitted.
Figure 15:
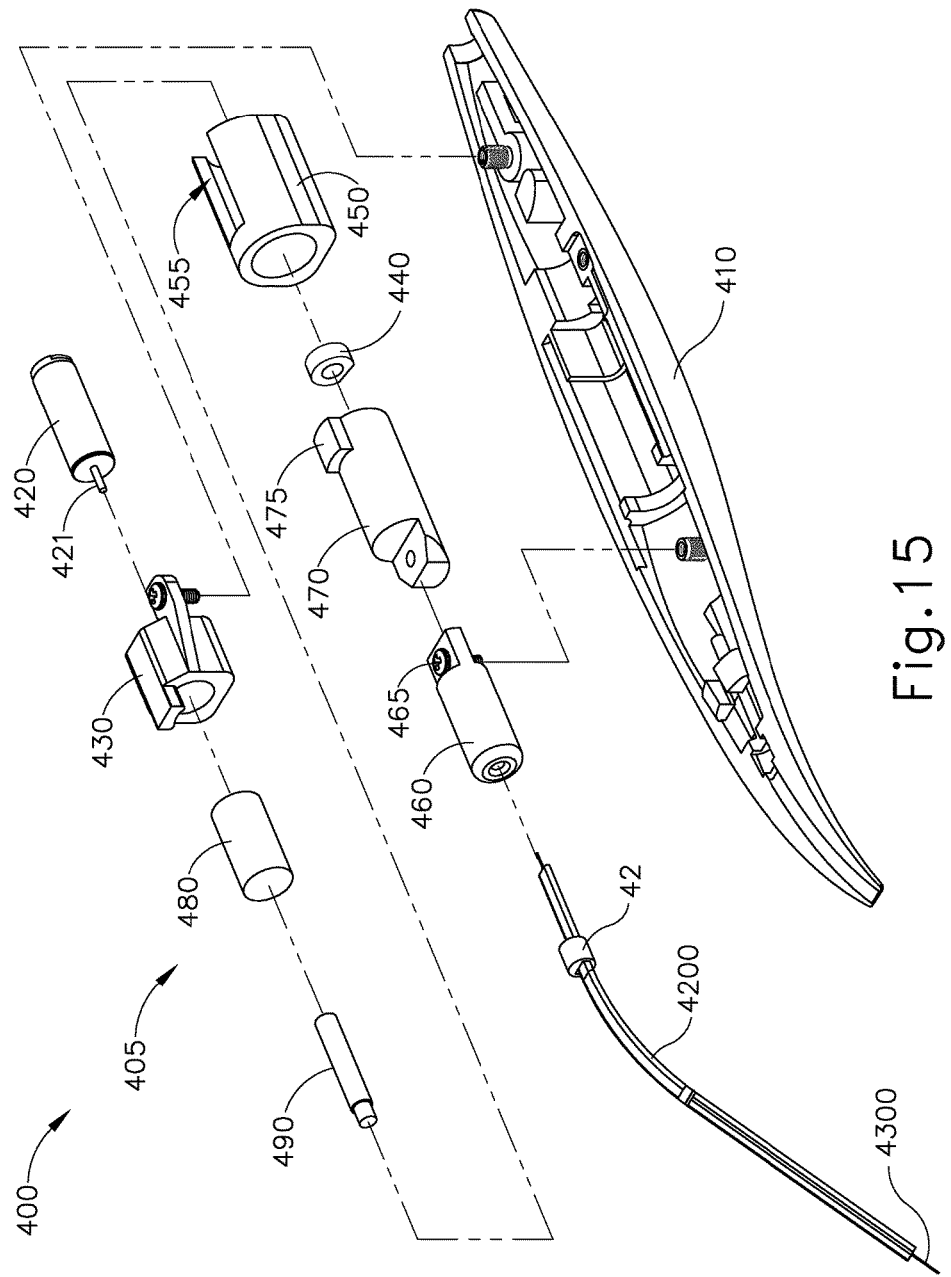
FIG. 15 depicts another exploded perspective view of the instrument of FIG. 12, with a top portion of the body omitted.

FIGS. 13-15 show different perspective views of instrument (400) without the top half of body (410) in order to display automatic actuation assembly (405). Automated actuation assembly (405) comprises motor (420), a motor mount (430), a gearbox (480), a lead screw (490), a motor nut (440), a translating body in the form of an actuator (470) with key (475), a bearing surface (450) with keyway (455), an actuating member such as a needle holder (460), an attachment member (465), and needle (4300). Gearbox (480) is secured to body (410) by motor mount (430).

Figure 16A:
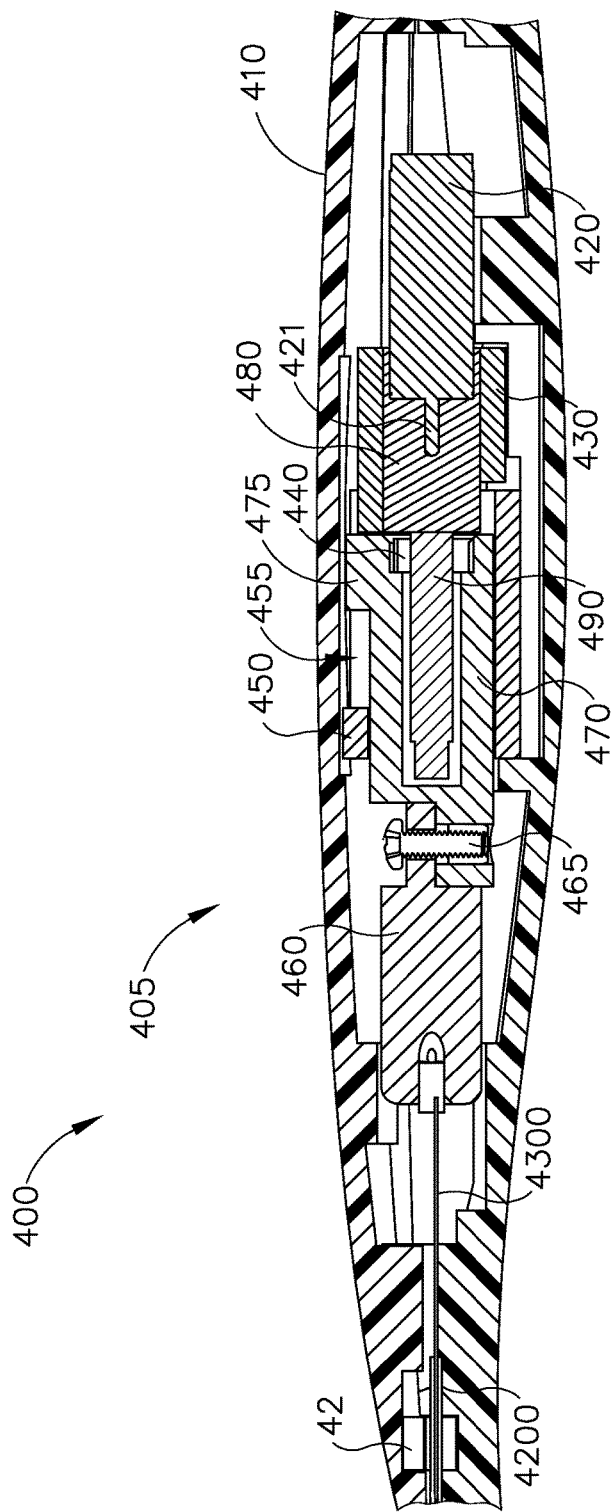
FIG. 16A depicts a side cross-sectional view of the instrument of FIG. 12, with the needle in a retracted position.
Figure 16B:
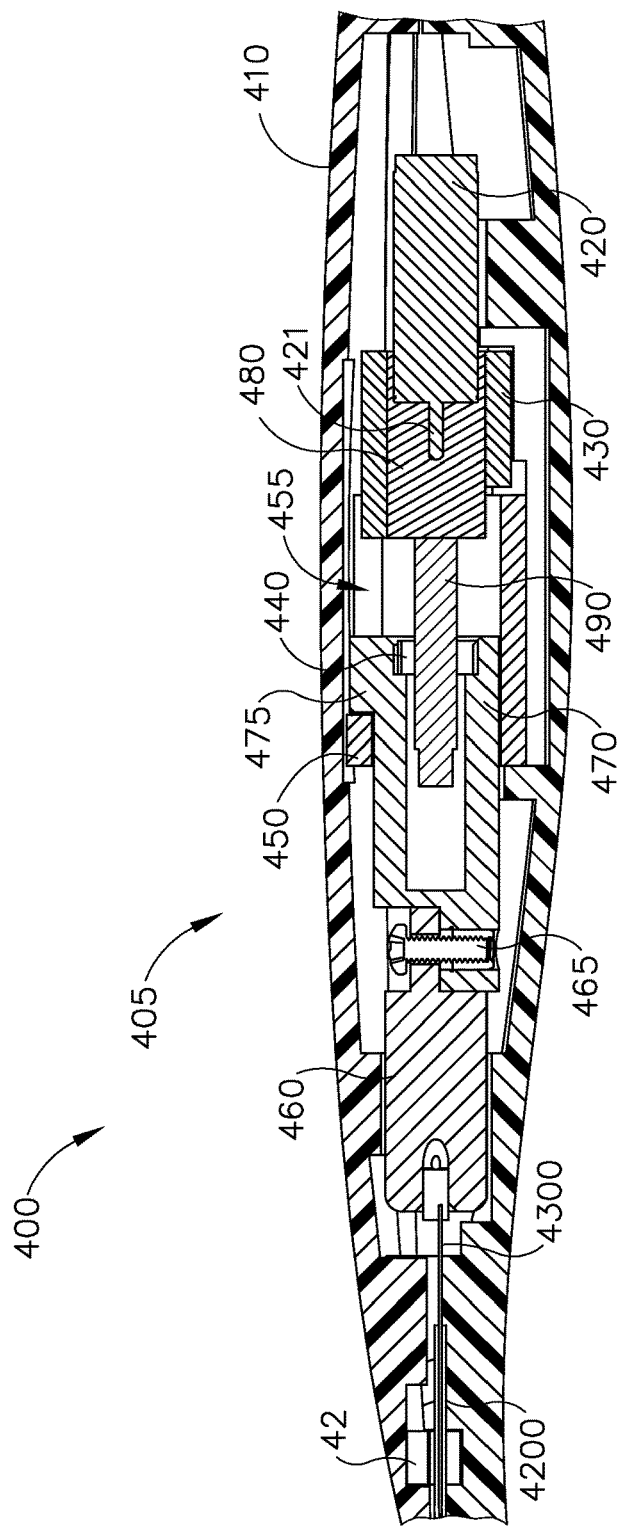
FIG. 16B depicts a side cross-sectional view of the instrument of FIG. 12, with the needle in an advanced position.

As seen in FIGS. 16A-B, an integral drive shaft (421) of motor (420) is rotatably coupled within the proximal end of gear box (480). The proximal end of lead screw (490) is rotatably coupled to the distal end of gear box (480). Gearbox (480) communicates the angular motion supplied by motor (420) and gearbox (480) to lead screw (490). If desirable, gearbox (480) may also manipulate the angular motion of motor (420), thereby giving lead screw (490) a smaller or greater angular velocity, torque, and/or other different characteristics compared to that supplied directly by drive shaft (421) of motor (420). Motor (420) is capable of rotating in a clockwise and counter clockwise direction in this example.

Lead screw (490) extends through the aperture of motor nut (440). Lead screw (490) and motor nut (440) are connected by complementary threading (not shown). The exterior surface of motor nut (440) is disposed within the proximal interior of actuator (470). The complementary shape of motor nut (440) and actuator (470) prevent the rotation of motor nut (440) when lead screw (490) rotates. Additionally, the dimensions of the exterior of motor nut (440) and the interior of actuator (470) are dimensioned for a tight fit so the force required to pull motor nut (440) apart from actuator (470) is greater than the force required to translate actuation assembly (405). Of course, other methods of attaching motor nut (440) and actuator (470) will be apparent to a person having ordinary skill in the art in view of the teachings herein.

As best seen in FIGS. 16A-B, when lead screw (490) rotates from the angular motion supplied by motor (420) through gear box (480), motor nut (440) is prevented from rotating because of actuator (470), thereby forcing motor nut (440) to travel along lead screw (490) by way of complementary threading (not shown). As motor nut (440) travels along complementary threading (not shown), actuator (470) moves along with motor nut (440). Thus, motor nut (440) and actuator (470) translate unitarily together, distally and proximally, in response to rotation of lead screw (490). The direction which motor nut (440) travels depends on the direction motor (420) rotates. In other words, motor (420) may be activated to drive lead crew (490) in a first angular direction to thereby drive actuator (470) from a proximal position (FIG. 16A) to a distal position (FIG. 16B); and then to drive lead screw (490) in a second angular direction to thereby drive actuator (470) from the distal position (FIG. 16B) back to the proximal position (FIG. 16A).

Figure 17A:
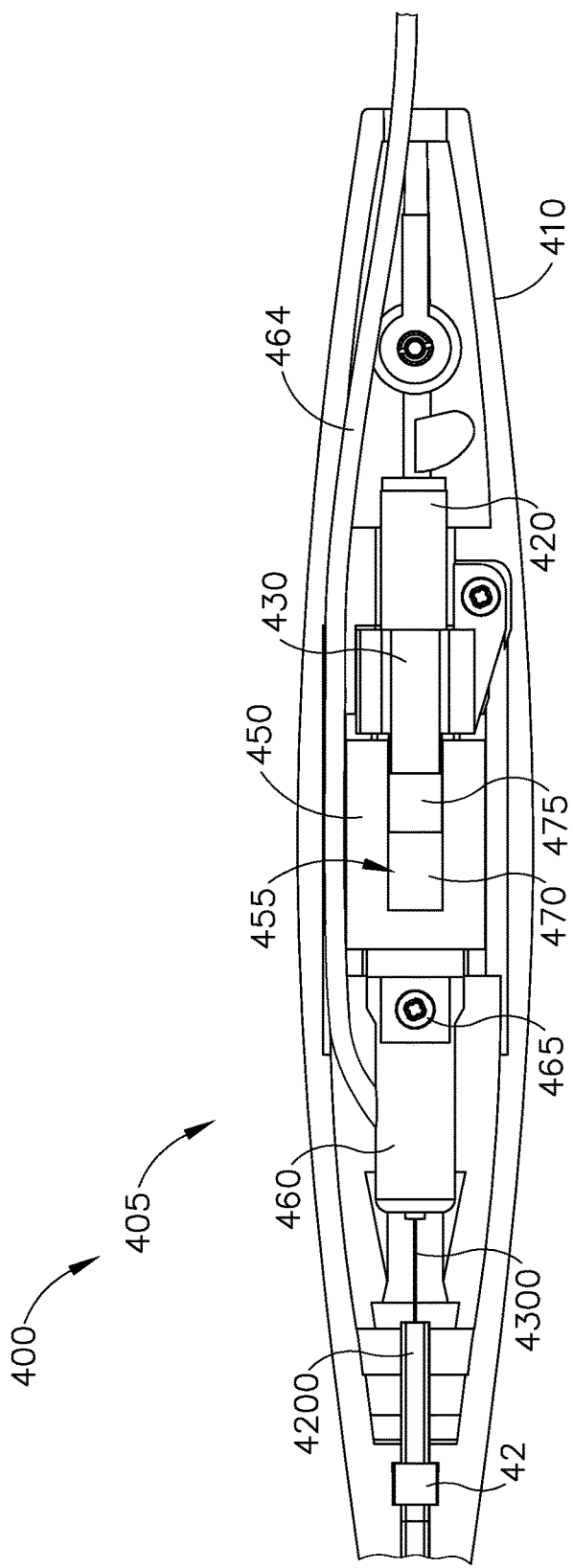
FIG. 17A depicts a top elevation view of the instrument of FIG. 12, with a top portion of the body omitted, and with the needle in the retracted position of FIG. 16A.
Figure 17B:
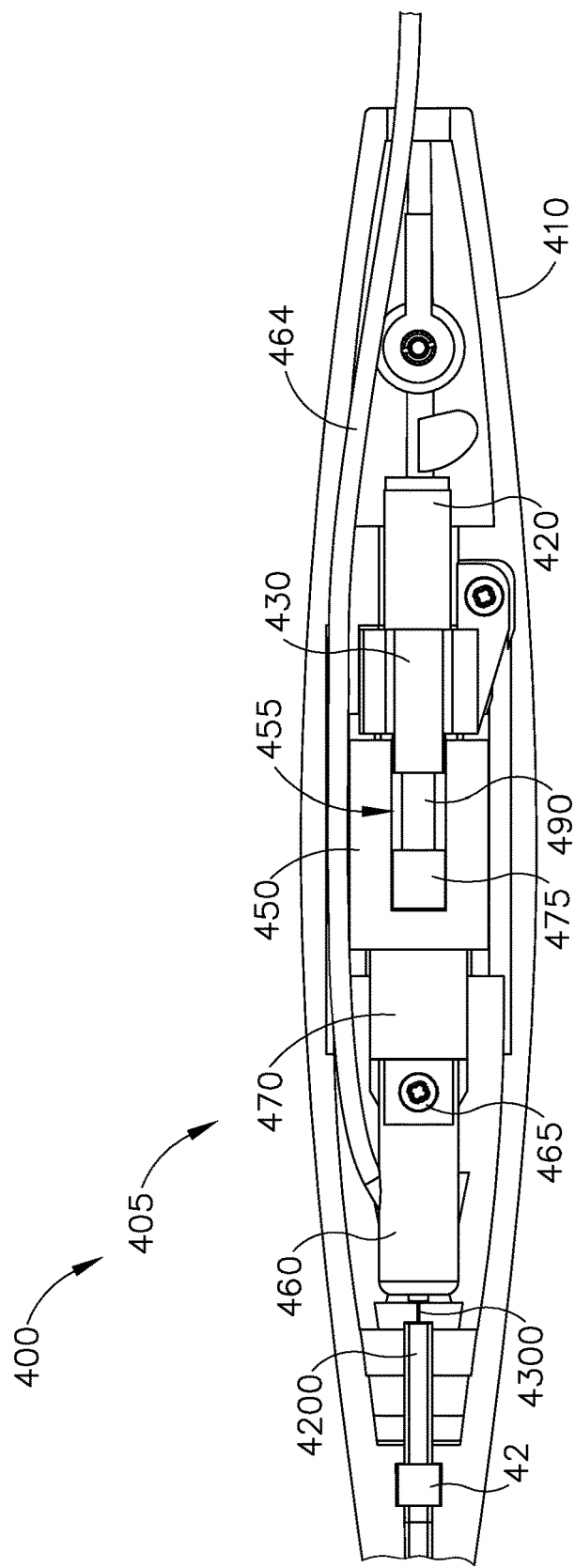
FIG. 17B depicts a top elevation view of the instrument of FIG. 12, with a top portion of the body omitted, and with a the needle in the advanced position of FIG. 16B.

As best seen in FIGS. 17A-B, actuator (470) is slidably disposed within bearing surface (450) with keyway (455). Bearing surface (450) with keyway (455) is disposed within body (410). Actuator (470) further comprises key (475), which fits within keyway (455). Key (475) fits within keyway (455) for two purposes: to prevent rotation of actuator (470) and to prevent actuator (470) from translating too far distally. The distal end of actuator (470) is connected to the proximal end of needle holder (460) via attachment member (465). The distal end of needle holder (460) is fixedly secured to needle (4300). Therefore, when actuator (470) translates either distally or proximally due to motor nut (440) (shown in FIGS. 14-16B) traveling along lead screw (490), needle (4300) translated distally or proximally as well. It should be noted that having actuator (470) and needle holder (460) as two separate units connected by attachment member (465) is entirely optional. Actuator (470) and needle holder (460) could be one integral unit rather than two separate pieces. In that case, there would be no need to attachment member (465).

Figure 18:
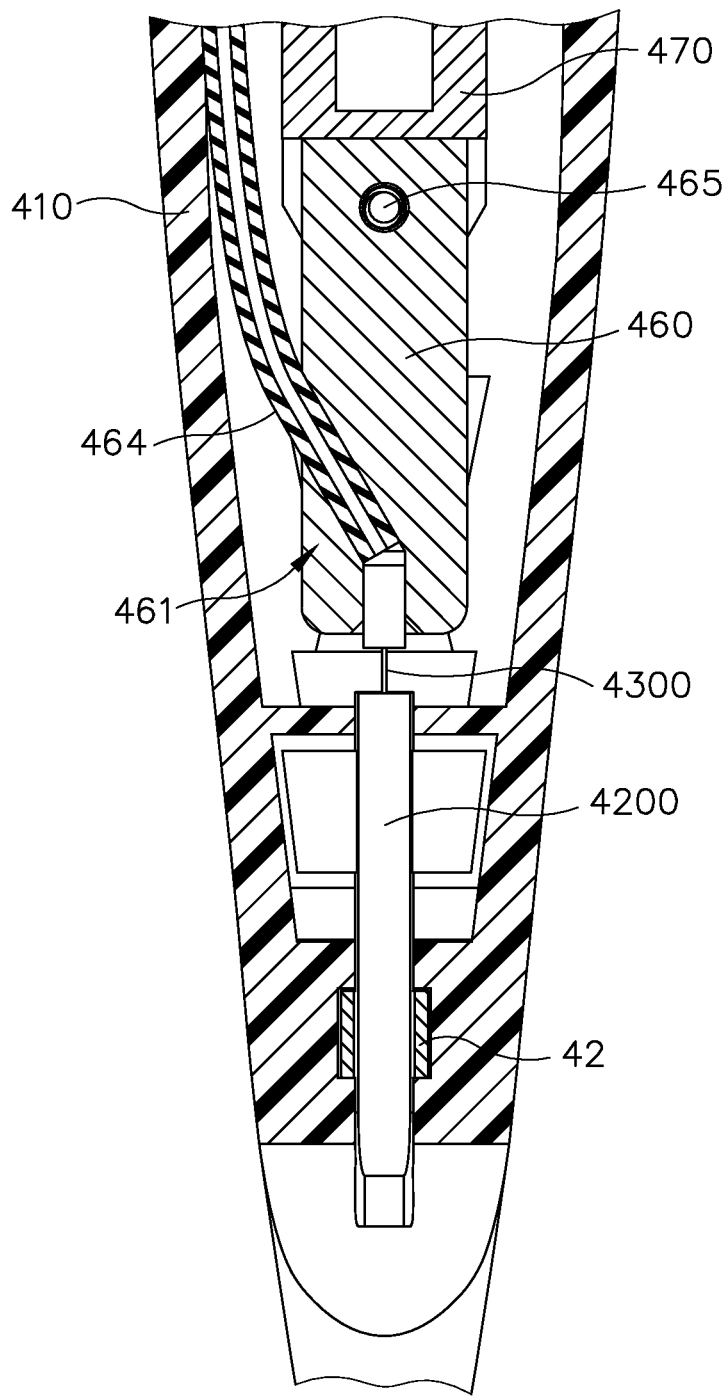
FIG. 18 depicts a top cross-sectional view of the distal end of the instrument of FIG. 12.

Instrument (400) of the present example further comprises a flexible supply tube (464). Flexible supply tube (464) is configured to supply needle (430) with fluid for leading bleb (340) and therapeutic agent (341) as described above to perform the subretinal administration of a therapeutic agent from a suprachoroidal approach (341) as described above. In this example, just one flexible supply tube (464) is utilized. Of course, multiple flexible supply tubes (464) could be utilized as would be apparent to a person having ordinary skill in the art in view of the teachings herein. As best seen in FIGS. 17A-B, flexible supply tube (464) comprises a distal end connected to needle holder (460), and a proximal end exiting the proximal end of body (410). As best seen in FIG. 18, needle holder (460) defines a hollow pathway (461) between the distal end of flexible supply tube (464) and the proximal end of needle (4300). Hollow pathway (461) provides a path for fluid communication from supply tube (464) to needle (4300). Needle holder (460) thus serves as a translating manifold for needle (4300). Needle holder (460) seals off hollow pathway (461) such that fluid communicated from supply tube (464) will only be further communicated through needle (4300). Flexible supply tube (464) is located on the peripheral of automated actuation assembly (405). The location of flexible supply tube (464) prevents unwanted interference during translation of automated actuation assembly (405).

Once needle (4300) is translated distally via automated actuation assembly (405) to the distal position (FIGS. 16B and 17B), fluid for leading bleb (340) and therapeutic agent (341) are supplied to needle (4300) via flexible supply tube (464) and hollow pathway (not shown) of needle holder (460) in accordance with the teachings above. Once therapeutic agent (341) has been successfully delivered as previously described above, motor (420) may then drive needle (4300) proximally back to the retracted position (FIGS. 16A and 17A). The operator may then remove flexible cannula (4200) from the eye of the patient, thereby completing the procedure.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for delivering therapeutic agent to an eye, wherein the apparatus comprises: (a) a body; (b) a cannula extending distally from the body, wherein the cannula is sized and configured to be insertable between a choroid and a sclera of a patient's eye, wherein the cannula defines a longitudinal axis; (c) a hollow needle, wherein the needle is slidable relative to the cannula; and (d) an actuation member, wherein the actuation member comprises: (i) an automated actuation assembly, and (ii) an activation element configured to activate the automated actuation assembly; wherein the automated actuation assembly is operable to actuate the needle relative to the cannula to thereby drive a distal portion of the needle along an exit axis that is obliquely oriented relative to the longitudinal axis of the cannula.

Example 2

The apparatus of Example 1, wherein the automated actuation assembly further comprises a motor communicatively coupled to the activation element.

Example 3

The apparatus of Example 2, wherein at least part of the automated actuation assembly is translatable relative to the body to actuate the needle.

Example 4

The apparatus of any one or more of Examples 2 through 3, wherein at least part of the automated actuation assembly is rotatable relative to the body to actuate the needle.

Example 5

The apparatus of Example 4, wherein the automated actuation assembly includes a threaded member and a threaded nut, wherein the threaded member is configured to engage the threaded nut to actuate the needle when the actuation member is rotated relative to the body.

Example 6

The apparatus of Example 5, wherein the automated actuation assembly further comprises a gearbox, wherein the motor is connected to the gearbox.

Example 7

The apparatus of Example 6, wherein the gearbox is also connected to the threaded member, wherein the gearbox is capable of communicating angular movement from the motor to the threaded member.

Example 8

The apparatus of any one or more of Examples 5 through 6, wherein the automated actuation assembly further comprises an actuating member, wherein the threaded nut is disposed within the actuating member in such a way to prevent rotation of the threaded nut, wherein translation in the actuating member translates the hollow needle.

Example 9

The apparatus of Example 8, wherein the rotation of the threaded member is configured to force the threaded nut along the threaded member, wherein the actuating member is configured to unitarily translate with the threaded nut.

Example 10

The apparatus of Example 9, wherein the automated actuation assembly further comprises a needle holder connected to the actuator, wherein the hollow needle is fixed to the needle holder.

Example 11

The apparatus of Example 10, wherein the needle holder is operable to provide a fluid coupling between a fluid source and the needle.

Example 12

The apparatus of any one or more of Examples 1 through 11, wherein the needle includes a sharp distal tip.

Example 13

The apparatus of Example 12, wherein the sharp distal tip of the needle comprises a first bevel, a second bevel, and a third bevel, wherein the first bevel, second bevel, and third bevel are each oriented obliquely relative to each other.

Example 14

The apparatus of any one or more of Examples 1 through 13, wherein the exit axis is oriented at an angle between approximately 5° and approximately 30° relative to the longitudinal axis of the cannula.

Example 15

The apparatus of any one or more of Examples 1 through 14, wherein the exit axis is oriented at an angle between approximately 7° and approximately 9° relative to the longitudinal axis of the cannula.

Example 16

The apparatus of any one or more of Examples 1 through 15, wherein the cannula includes a beveled distal end, wherein the beveled distal end has a bevel angle, wherein the bevel angle is between approximately 10° and approximately 30°.

Example 17

The apparatus of any one or more of Examples 1 through 16, wherein the cannula defines a plurality of lumens extending longitudinally through the length of the cannula, wherein at least one lumen of the plurality of lumens is configured to slidably receive the needle.

Example 18

The apparatus of any one or more of Examples 1 through 17, wherein the cannula has a flexural stiffness between $2.0 \times 10^{-6}$ Nm$^2$ and $6.0 \times 10^{-6}$ Nm$^2$.

Example 19

An apparatus for delivering therapeutic agent to an eye, wherein the apparatus comprises: (a) a body; (b) a cannula extending distally from the body, wherein the cannula is sized and configured to be insertable between a choroid and a sclera of a patient's eye, wherein the cannula defines a longitudinal axis; (c) a hollow needle, wherein the needle is slidable relative to the cannula; and (d) an actuation member, wherein the actuation member comprises: (i) an activation element, and (ii) a motor disposed within the body communicatively coupled with the activation element, wherein the actuation member is operable to actuate the needle relative to the cannula to thereby drive a distal portion of the needle along an exit axis that is obliquely oriented relative to the longitudinal axis of the cannula.

Example 20

An apparatus for delivering therapeutic agent to an eye, wherein the apparatus comprises: (a) a body; (b) a cannula extending distally from the body, wherein the cannula is sized and configured to be insertable between a choroid and a sclera of a patient's eye, wherein the cannula defines a longitudinal axis; (c) a hollow needle, wherein the needle is slidable relative to the cannula; and (d) an actuation member, wherein the actuation member comprises: (i) a motor disposed within the body, wherein the motor comprises a distal end, (ii) a gearbox comprising a distal end and a proximal end, wherein the proximal end of the gear box is connected to the distal end of the motor, (iii) a threaded rod comprising a proximal end and a distal end, wherein the proximal end of the threaded rod is connected to the gearbox, wherein the threaded rod includes threading, and (iv) a motor nut, wherein the motor nut surrounds the threaded rod, wherein the motor nut comprises threading complementing the threading of the threaded rod, wherein the motor nut is configured to translate on the threaded rod in response to the rotation of the motor, wherein the actuation member is operable to actuate the needle relative to the cannula to thereby drive a distal portion of the needle along an exit axis that is obliquely oriented relative to the longitudinal axis of the cannula VII. Miscellaneous It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for delivering therapeutic agent to an eye, wherein the apparatus comprises:
   (a) a body;
   (b) a cannula extending distally from the body, wherein the cannula is sized and configured to be insertable between a choroid and a sclera of a patient's eye, wherein the cannula defines a longitudinal axis;
   (c) a hollow needle comprising a proximal end, wherein the needle is slidable relative to the cannula; and
   (d) an actuation member, wherein the actuation member comprises:
      (i) an automated actuation assembly comprising a motor and an actuating member, wherein the actuating member is coupled to the proximal end of the hollow needle such that the actuating member is translatable to thereby translate the hollow needle, wherein the actuating member defines a hollow pathway in fluid communication with the distal end of the hollow needle, and (ii) an activation element configured to activate the automated actuation assembly;

wherein the motor is operable to actuate the actuating member and the needle relative to the cannula to thereby drive a distal portion of the needle along an exit axis that is obliquely oriented relative to the longitudinal axis of the cannula.

2. The apparatus of claim 1, wherein the motor is communicatively coupled to the activation element.

3. The apparatus of claim 2, wherein at least part of the automated actuation assembly is translatable relative to the body to actuate the needle.

4. The apparatus of claim 2, wherein at least part of the automated actuation assembly is rotatable relative to the body to actuate the needle.

5. The apparatus of claim 4, wherein the automated actuation assembly includes a threaded member and a threaded nut, wherein the threaded member is configured to engage the threaded nut to actuate the needle when the actuation member is rotated relative to the body.

6. The apparatus of claim 5, wherein the automated actuation assembly further comprises a gearbox, wherein the motor is connected to the gearbox.

7. The apparatus of claim 6, wherein the gearbox is also connected to the threaded member, wherein the gearbox is capable of communicating angular movement from the motor to the threaded member.

8. The apparatus of claim 5, wherein the automated actuation assembly further comprises a translating body wherein the threaded nut is disposed within the translating body in such a way to prevent rotation of the threaded nut.

9. The apparatus of claim 8, wherein the rotation of the threaded member is configured to force the threaded nut along the threaded member, wherein the translating body is configured to unitarily translate with the threaded nut.

10. The apparatus of claim 9, wherein the translating body is fixed to the actuating member.

11. The apparatus of claim 1, further comprising a fluid source in fluid communication with the proximal end of the hollow needle.

12. The apparatus of claim 1, wherein the needle includes a sharp distal tip.

13. The apparatus of claim 12, wherein the sharp distal tip of the needle comprises a first bevel, a second bevel, and a third bevel, wherein the first bevel, second bevel, and third bevel are each oriented obliquely relative to each other.

14. The apparatus of claim 1, wherein the exit axis is oriented at an angle between approximately 5° and approximately 30° relative to the longitudinal axis of the cannula.

15. The apparatus of claim 1, wherein the exit axis is oriented at an angle between approximately 7° and approximately 9° relative to the longitudinal axis of the cannula.

16. The apparatus of claim 1, wherein the cannula includes a beveled distal end, wherein the beveled distal end has a bevel angle, wherein the bevel angle is between approximately 10° and approximately 30°.

17. The apparatus of claim 1, wherein the cannula defines a plurality of lumens extending longitudinally through the length of the cannula, wherein at least one lumen of the plurality of lumens is configured to slidably receive the needle.

18. The apparatus of claim 1, wherein the cannula has a flexural stiffness between $2.0 \times 10^{-6}$ Nm$^2$ and $6.0 \times 10^{-6}$ Nm$^2$.

19. An apparatus for delivering therapeutic agent to an eye, wherein the apparatus comprises:

(a) a first body;

(b) a cannula extending distally from the first body, wherein the cannula is sized and configured to be insertable between a choroid and a sclera of a patient's eye, wherein the cannula defines a longitudinal axis;

(c) a hollow needle, wherein the needle is slidable relative to the cannula; and (d) an actuation member, wherein the actuation member comprises:

(i) an activation element, (ii) a motor disposed within the first body communicatively coupled with the activation element, (iii) a translating body, wherein the motor is configured to linearly drive the translating body, wherein the translating body comprises a key, and (iv) a bearing surface fixed relative to the first body, wherein the bearing surface defines a keyway, wherein the key of the translating body is slidably housed within the keyway such that the translating body is rotationally fixed relative to the bearing surface, wherein the actuation member is operable to actuate the needle relative to the cannula to thereby drive a distal portion of the needle along an exit axis that is obliquely oriented relative to the longitudinal axis of the cannula.

20. An apparatus for delivering therapeutic agent to an eye, wherein the apparatus comprises:

(a) a body;

(b) a cannula extending distally from the body, wherein the cannula is sized and configured to be insertable between a choroid and a sclera of a patient's eye, wherein the cannula defines a longitudinal axis;

(c) a hollow needle comprising an open proximal end, wherein the needle is slidable relative to the cannula; and (d) an actuation member, wherein the actuation member comprises:

(i) a motor disposed within the body, wherein the motor comprises a distal end, (ii) a gearbox comprising a distal end and a proximal end, wherein the proximal end of the gear box is connected to the distal end of the motor, (iii) a threaded rod comprising a proximal end and a distal end, wherein the proximal end of the threaded rod is connected to the gearbox, wherein the threaded rod includes threading, (iv) a motor nut, wherein the motor nut surrounds the threaded rod, wherein the motor nut comprises threading complementing the threading of the threaded rod, wherein the motor nut is configured to translate on the threaded rod in response to the rotation of the motor, and (v) an actuating member coupled with the motor nut and the proximal end of the hollow needle, wherein the actuating member is in fluid communication with the open proximal end of the hollow needle, wherein the actuation member is operable to actuate the needle relative to the cannula to thereby drive a distal portion of the needle along an exit axis that is obliquely oriented relative to the longitudinal axis of the cannula.

* * * * *